(12) United States Patent
Yoshii et al.

(10) Patent No.: US 6,358,984 B1
(45) Date of Patent: Mar. 19, 2002

(54) 2,4-DIOXOPYRROLIDINE AND 2,4-DIOXOTETRAHYDROFURAN DERIVATIVES AND MEDICINES CONTAINING THE SAME AS THE ACTIVE INGREDIENT

(75) Inventors: Eiichi Yoshii; Masao Mori, both of Toyama (JP)

(73) Assignee: Lead Chemical Co., Ltd., Toyama (JP)

( * ) Notice: Subject to any disclaimer, the term of this patent is extended or adjusted under 35 U.S.C. 154(b) by 0 days.

(21) Appl. No.: 09/637,613

(22) Filed: Aug. 11, 2000

Related U.S. Application Data

(62) Division of application No. 09/254,685, filed as application No. PCT/JP97/03274 on Sep. 17, 1997, now Pat. No. 6,232,335.

(30) Foreign Application Priority Data

Sep. 18, 1996 (JP) .............................. 8-268014

(51) Int. Cl.[7] .................. A61K 31/4196; C07D 407/10
(52) U.S. Cl. ................. 514/383; 548/266.2; 548/266.6
(58) Field of Search ....................... 514/383; 548/266.2, 548/266.6

(56) References Cited

U.S. PATENT DOCUMENTS

| 4,340,598 A | 7/1982 | Furukawa et al. |
| 4,355,040 A | 10/1982 | Furukawa et al. |

FOREIGN PATENT DOCUMENTS

| JP | A-3-128365 | 5/1991 |
| JP | A-5-286948 | 11/1993 |
| JP | A-6-80629 | 3/1994 |
| WO | WO 89/06233 | 7/1989 |
| WO | WO 91/17148 | 11/1991 |
| WO | WO 91/18888 | 12/1991 |

OTHER PUBLICATIONS

Ondetti, Miguel A. et al., "Chapter 9: Inhibitors of the Renin–Angiotensin System," Annual Reports in Medicinal Chemistry–13, 1978, pp. 82–91.
Carini, David J. et al., "Nonpeptide Angiotensin II Receptor Antagonists: The Discovery of a Series of N–(Biphenylylmethyl)imidazoles as Potent, Orally Active Antihypertensives," J. Med. Chem., vol. 34, 1991, pp. 2525–2547.
Mederski, Werner E. K. R. et al., "Non–Peptide Angiotensin II Receptor Antagonists: Synthesis and Biological Activity of a Series of Novel 4,5–Dihydro–4–oxo–3H–imidazo{4,5–c}pyridine Derivatives," J. Med. Chem., vol. 37, 1994, pp. 1632–1645.
Kubo, Keiji et al., "Nonpeptide Angiotensin II Receptor Antagonists: Synthesis and Biological Activity of Benzimidazoles," J. Med. Chem., vol. 36, 1993, pp. 1772–1784.
Bradbury, Robert H. et al., "New Nonpeptide Angiotensin II Receptor Antagonists: @. Synthesis, Biological Properties, and Structure–Activity Relationships of 2–Alkyl–4–(biphenylylmethoxy)quinoline Derivatives," J. Med. Chem., vol. 35, 1992, pp. 4027–4038.
Ashton, Wallace T. et al., "Nonpeptide Angiotensin II Antagonists Derived from 1H–Pyrazole–5–carboxylates and 4–Aryl–1H–imidazole–5–carboxylates," J. Med. Chem., vol. 36, 1993, pp. 2595–3605.
Ashton, Wallace T. et al., "Nonpeptide Angiotensin II Antagonists Derived from 4H–1,2,4–Triazoles and 3H–Imidazo{1,2–b}{1,2,4}triazoles," J. Med. Chem., vol. 36, 1993, pp. 591–609.
Atwal, Karnail S. et al., "Dihydropyrimidine Angiotensin II Receptor Antagonists," J. Med. Chem., vol. 35, 1992, pp. 4751–4763.
Henning, Hans–Georg et al., "Advances in Tetramic Acid Chemistry," Advances in Heterocyclic Chemistry, vol. 57, 1993, pp. 139–185.
Pattenden, G., "Natural 4–Ylidenebutenolides and 4–Ylidenetronic Acids," Progress in the Chemistry of Organic Natural Products, vol. 35, 1978, pp. 133–198.
Bradbury, Robert H. et al., "New Nonpeptide Angiotensin II Receptor Antagonists: 3. Synthesis, Biological Properties, and Structure–Activity Relationships of 2–Alkyl–4–(biphenylylmethoxy)Pyridine Derivatives," J. Med. Chem., vol. 36, 1993, pp. 1245–1254.

*Primary Examiner*—Patricia L. Morris
(74) *Attorney, Agent, or Firm*—Oliff & Berridge, PLC

(57) ABSTRACT

Compounds including 1-(biphenyl-4-yl)methyl-1H-1,2,4-triazoles and 1-(biphenyl-4-yl)methyl-4H-1,2,4-triazoles each having a (2,4-dioxopyrrolidine-5-ylidene) methyl or (2,4-dioxo-tetrahydrofuran-5-ylidene)methyl group as the substituent at the 2'-position and salts thereof are lowly toxic and highly safe and are useful as an angiotensin II antagonist. Thus, these compounds can be used in medicines, which contain these compounds as an active ingredient.

5 Claims, No Drawings

2,4-DIOXOPYRROLIDINE AND 2,4-DIOXOTETRAHYDROFURAN DERIVATIVES AND MEDICINES CONTAINING THE SAME AS THE ACTIVE INGREDIENT

This is a Division of application Ser. No. 09/254,685 filed Mar. 17, 1999 (U.S. National Stage of PCT/JP97/03274, filed Sep. 17, 1997), which issued as U.S. Pat. No. 6,232,335 May 15, 2001. The entire disclosure of the prior application(s) is hereby incorporated by reference herein in its entirety.

TECHNICAL FIELD

The present invention relates to a novel 2,4-dioxopyrrolidine derivative and a novel 2,4-dioxotetrahydrofuran derivative having excellent pharmacological effects, and their salts, and medicines containing these compounds as active ingredients.

More particularly, the present invention relates to novel 1-(biphenyl-4-yl)methyl-1H-1,2,4-triazoles and 1-(biphenyl-4-yl)methy-4H-1,2,4-triazoles having a (2,4-dioxopyrrolidine-5-ylidene)methyl group or (2,4-dioxotetrahydrofuran-5-ylidene)methyl group at the 2'-position as a substituent, and their salts, which are useful as therapeutic agent for circulatory system disease, e.g. hypertension and/or diseases such as heart and renal diseases that are caused by the action of angiotensin II, due to their strong angiotensin II receptor antagonism and antihypertensive effect, and to medicines containing these compounds as active ingredient.

BACKGROUND ART

The renin-angiotensin system plays an important role in vivo, in maintaining homeostasis for systemic blood, humoral amount and electrolyte balance.

The results of research on angiotensin II receptor antagonists, angiotensin II converting enzyme inhibitors, and renin inhibitors suggest strongly that the renin-angiotensin system is involved in the mechanism for the manifestation of hypertension. Angiotensin II converting enzyme inhibitors (ACE inhibitors) such as captopril and enalapril are effective in the treatment of hypertension or heart failure and already widely used.

An ACE inhibitor, however, affects the metabolic pathway of bradykinin or substance P, thereby inducing side effects such as dry cough or vascular edema being associated with the accumulation of these peptides. On the other hand, an angiotensin II receptor antagonist can restrain only the effects of angiotensin II, so it is expected to minimize the side effects. Peptidic antagonist such as saralisin in the angiotensin II receptor antagonists is firmly bounded with the receptor, but due to its short half-life in the human body, it is inappropriate for oral administration [M. A. Ondatti and D. W. Cushman, Annual Reports in Medical Chemistry 13, 82–91 (1978)].

Under these circumstances, a non-peptidic angiotensin II receptor antagonist has been developed, though its activity is not so strong (U.S. Pat. No. 4,340,598, U.S. Pat. No. 4,355,040). A series of biphenylimidazole compounds have been reported to be as angiotensin II receptor antagonists which are non-peptidic, very effective and selective and as what exhibit antihypertensive effect in oral administration [D. J. Carini at al., J. Med. Chem. 34, 2525–2547 (1991)]. It has also been suggested that the presence of an acidic group at the 2'-position of a biphenyl group is important for binding with the angiotensin II receptor. A hydrophobic tetrazole group has been selected as an acidic group that is appropriate for oral administration and has a high bioavailability, and DUP-753 is known as a biphenylimidazole compound having a tetrazole group at the 2'-position.

Imidazolepyridine [W. W. K. R. Mederski et al., J. Med. Chem. 37, 1632 to 1645 (1994)]; benzimidazole [K. Kubo et al., J. Med. Chem. 36, 1772 to 1784 (1993)], quinoline (R. H. Bradbury et al., J. Med. Chem. 35, 4027 to 4038 (1992)), pyrazole [W. T. Ashton et al., J. Med. Chem. 36, 3595 to 3605 (1993)], triazole [W. T. Ashton et al., J. Med. Chem. 36, 591 to 609 (1993), PCT/US91/02926], pyrimidine [K. S. Atwel et al., J. Med. Chem. 35, 4751 to 4763 (1993)], and pyridine [R. H. Bradbury et al., J. Med. Chem. 36, 1245 to 1254 (1993)], have been disclosed as the alternative to an imidazole ring constituting the imidazole compound. Of these compounds, 1,2,4-triazole is preferable, because it is a heterocyclic ring geometrically similar to the imidazole ring, and the G.D. Searle & Co. has disclosed SC-50560 with 1H-1,2,4-triazole as a superior compound having a strong angiotensin II receptor antagonism (PCT/US91/02926).

2,4-dioxopyrrolidine (called as tetraic acid, too) and 2,4-dioxotetrahydrofuran (called as tetronic acid, too) are known as components of the chemical structure of a certain physiologically active substance of natural origin [H. G. Henning and A. Gelbin, Advance in Heterocyclic Chemistry vol. 57, pp. 139 (1993), Academic Press, Inc., G. Pattanden, Progress in the Chemistry of Organic Natural Products Vol. 35, pp. 133 (1978)]. Such a heterocyclic group is easily presumed to fit with a hydrophobic pocket in a binding site of an organism that is required for the manifestation of physiological activity of a substance having the heterocyclic group as a component, and to play an important role as an acid component and expected to have, in the angiotensin II receptor antagonist too, that is a sufficient possibility as a bio-isostere for the tetrazole ring of the DUP-763.

Thus, the present inventors have synthesized a 2,4-dioxopyrrolidine derivative and a 2,4-dioxohydrofuran derivative and researched the angiotensin II receptor antagonism to find compounds having significant effects as new non-peptidic angiotensin II receptor antagonists as described hereinafter.

DISCLOSURE OF THE INVENTION

The present invention relates to a compound of the following formula (I) or its salt:

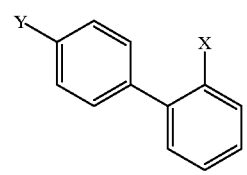

(I)

wherein X is a group of the following formula (II) or (III):

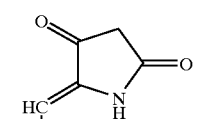

(II)

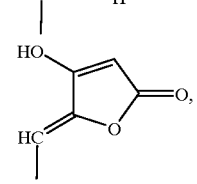

(III)

Y is a group of the following formula (IV) or (V):

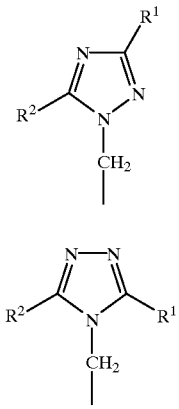

(IV)

(V)

R$^1$ and R$^2$ independently represent a hydrogen atom, an alkyl group having 1 to 6 carbon atoms, a haloalkyl group having 1 to 6 carbon atoms, a cycloalkyl group having 3 to 6 carbon atoms, an aryl group, a halogenated aryl group, an aralkyl group, or a heterocyclic group containing at least one ring atom selected from an oxygen atom, a sulfur atom and a nitrogen atom.

The compound of the formula (I) is:

(1) a compound of the following formula (I-a) or its salt:

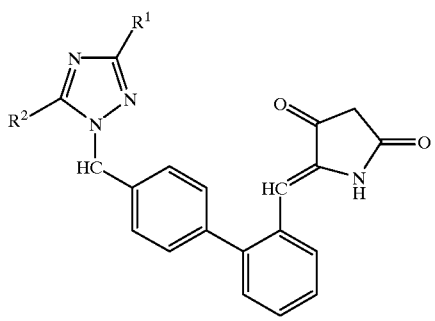

(I-a)

wherein X is a group of the formula (II) and Y is a group of the formula (IV);

(2) a compound of the following formula (I-b) or its salt:

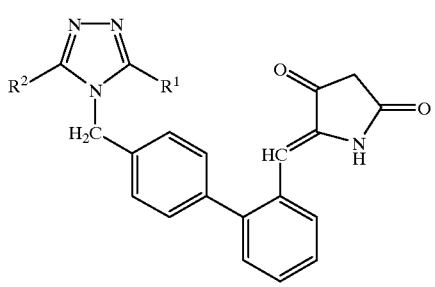

(I-b)

wherein X is a group of the formula (II) and Y is a group of the formula (V);

(3) a compound of the following formula (I-c) or its salt:

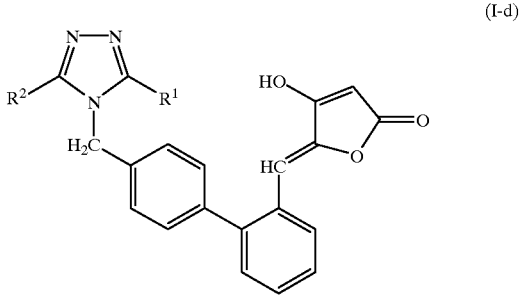

(I-c)

wherein X is a group of the formula (III) and Y is a group of the formula (IV), or (4) a compound of the following formula (I-d) or its salt:

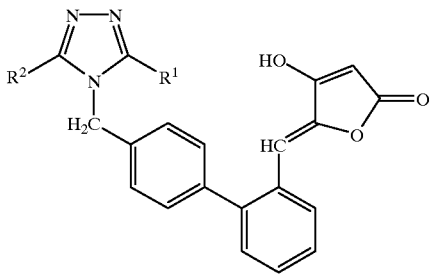

(I-d)

wherein X is a group of the formula (III) and Y is a group of the formula (V).

The alkyl group having 1 to 6 carbon atoms that is included in the definition of the substituent may be a straight chain or branched one, and for example, a methyl group, an ethyl group, a n-propyl group, an isopropyl group, a n-butyl group, an isobutyl group, a tert-butyl group, a pentyl group, or a hexyl group may be mentioned an preferable one. In particular, an alkyl group such as a n-propyl group, an isopropyl group or a n-butyl group may be mentioned preferably.

The haloalkyl group having 1 to 6 carbon atoms is an alkyl group mono- or poly-substituted by halogen atoms, and is, for example, a fluoromethyl group, difluoromethyl group, trifluoromethyl group, chloromethyl group, dichloromethyl group, trichloromethyl group, 2,2,2-trifluoroethyl group, 2-fluoroethyl group, 2-chloroethyl group, 2,2,2-trichloroethyl group, 1,1-difluoroethyl group, 1,1-difluoropropyl group, 1,1-difluorobutyl group or 1,1-difluoropentyl group, or the like.

The cycloalkyl group is, for example, a cyclopropyl group, cyclobutyl group, cyclopentyl group or cyclohexyl group, or the like and a cyclopropyl group is preferable one.

As the aryl and halogenated aryl groups, a phenyl group, 2-fluorophenyl group or 4-fluorophenyl group, or the like is preferable one and, as the aralkyl group a phenylmethyl group or 2-phenylethyl group, or the like is preferable one.

The heterocyclic group containing at least one ring atom selected from an oxygen atom, a sulfur atom or a nitrogen atom is a furyl group, thienyl group or pyridyl group, or the like, and the preferable heterocyclic group is a furan-2-yl group, thiophene-2-yl group and pyridine-4-yl group.

As the specific compounds belonging to the above formula (I-a), the following group of compounds can be mentioned:

1-[2'-[(2,4-dioxopyrrolidine-5(Z)-ylidene)methyl]
biphenyl-4-yl]methyl-1H-1,2,4-triazole;

3,5-dipropyl-1-[2'-[(2,4-dioxopyrrolidine-5(Z)-ylidene)
methyl]biphenyl-4-yl]methyl-1H-1,2,4-triazole;

3,5-diisopropyl-1-[2'-[(2,4-dioxopyrrolidine-5(Z)-
ylidene)methyl]biphenyl-4-yl]methyl-1H-1,2,4-
triazole;

5-butyl-3-cyclopropyl-1-[(2'-[(2,4-dioxopyrrolidine-5
(Z)-ylidene)methyl]biphenyl-4-yl]methyl-1H-1,2,4-
triazole;

3,5-dibutyl-1-[2'-[(2,4-dioxopyrrolidine-5(Z)-ylidene)
methyl]biphenyl-4-yl]methyl-1H-1,2,4-triazole;

5-butyl-3-(1,1-difluoropropyl)-1-[2'-[2,4-
dioxopyrrolidine-5(Z)-ylidene)methyl]biphenyl-4-yl]
methyl-1H-1,2,4-triazole;

5-butyl-3-phenyl-1-[2'-[(2,4-dioxopyrrolidine- 5(Z)-
ylidene)methyl]biphenyl-4-yl]methyl-1H-1,2,4-
triazole;

5-butyl-3-(2-phenylethyl)-1-[2'-[(2,4-dioxopyrrolidine-5
(Z)-ylidene)methyl]biphenyl-4-yl]methyl-1H-1,2,4-
triazole;

5-butyl-3-(4-fluorophenyl)-1-[2'-[(2,4-dioxopyrrolidine-
5(Z)-ylidene)methyl]biphenyl-4-yl]methyl-1H-1,2,4-
triazole;

5-butyl-3-(2-fluorophenyl)-1-[2'-[(2,4-dioxopyrrolidine-
5(Z)-ylidene)methyl]biphenyl-4-yl]methyl-1H-1,2,4-
triazole;

5-butyl-3-(4-pyridyl)-1-[2'-[(2,4-dioxopyrrolidine-5(Z)-
ylidene)methyl]biphenyl-4-yl]methyl-1H-1,2,4-
triazole;

5-butyl-3-(2-furyl)-1-[2'-[(2,4-dioxopyrrolidine-5(Z)-
ylidene)methyl]biphenyl-4-yl]methyl-1H-1,2,4-
triazole;

5-butyl-3-(thiophene-2-yl)-1-[2'-[(2,4-dioxopyrrolidine-5
(Z)-ylidene)methyl]biphenyl-4-yl]methyl-1H-1,2,4-
triazole.

As the specific compounds belonging to the above formula (I-b), the following group of compounds mentioned:

1-[2'-[(2,4-dioxopyrrolidine-5(Z)-ylidene)methyl]
biphenyl-4-yl]methyl-4H-1,2,4-triazole;

3,5-dipropyl-1-[2'-[(2,4-dioxopyrrolidine-5(Z)-ylidene)
methyl]biphenyl-4-yl]methyl-4H-1,2,4-triazole;

3,5-diisopropyl-1-[2'-[(2,4-dioxopyrrolidine-5(Z)-
ylidene)methyl]biphenyl-4-yl]methyl-4H-1,2,4-
triazole;

5-butyl-3-cyclopropyl-1-[2'-[(2,4-dioxopyrrolidine-5(Z)-
ylidene)methyl]biphenyl-4-yl]methyl-4H-1,2,4-
triazole;

3,5-dibutyl-1-[2'-[(2,4-dioxopyrrolidine-5(Z)-ylidene)
methyl]biphenyl-4-yl]methyl-4H-1,2,4-triazole;

5-butyl-3-(1,1-difluoropropyl)-1-[2'-[(2,4-
dioxopyrrolidine-5(Z)-ylidene)methyl]biphenyl-4-yl
methyl-4H-1,2,4-triazole;

5-butyl-3-phenyl-1-[2'-[(2,4-dioxopyrrolidine-5(Z)-
ylidene)methyl]biphenyl-4-yl]methyl-4H-1,2,4-
triazole;

5-butyl-3-phenyl-(2-phenylethyl)-1-[2'-[(2,4-
dioxopyrrolidine-5(z)-ylidene)methyl]biphenyl-4-yl]
methyl-4H-1,2,4-triazole;

5-butyl-3-(4-fluorophenyl)-1-[2'-[(2,4-dioxopyrrolidine-
5(Z)-ylidene)methyl]biphenyl-4-yl]methyl-4H-1,2,4-
triazole;

5-butyl-3-(2-fluorophenyl)-1-[2'-[(2,4-dioxopyrrolidine-
5(Z)-ylidene)methyl]biphenyl-4-yl]methyl-4H-1,2,4-
triazole;

5-butyl-3-(4-pyridyl)-1-[2'-[(2,4-dioxopyrrolidine-5(Z)-
ylidene)methyl]biphenyl-4-yl]methyl-4H-1,2,4-
triazole;

5-butyl-3-(2-furyl)-1-[2'-[(2,4-dioxopyrrolidine-5(Z)-
ylidene)methyl biphenyl-4-yl]methyl-4H-1,2,4-triazole;

5-butyl-3-(thiophene-2-yl)-1-[2'-[(2,4-dioxopyrrolidine-5
(Z)-ylidene)methyl]biphenyl-4-yl]methyl-4H-1,2,4-
triazole.

As the specific compounds belonging to the above formula (I-c), the following group of compounds can be mentioned:

1-[2'-[(4-hydroxy-2(5H)-furanone-5(Z)-ylidene)methyl]
biphenyl-4-yl]methyl-1H-1,2,4-triazole;

3,5-dipropyl-1-[2'-[(4-hydroxy-2(5H)-furanone-5(Z)-
ylidene)methyl]biphenyl-4-yl]methyl-1H-1,2,4-
triazole;

3,5-diisopropyl-1-[2'-[(4-hydroxy-2(5H)-furanone-5(Z)-
ylidene)methyl]biphenyl-4-yl]methyl-1H-1,2,4-
triazole;

5-butyl-3-cyclopropyl-1-[2'-[(4-hydroxy-2(5H)-
furanone-5(Z)-ylidene)methyl]biphenyl-4-yl]methyl-
1H-1,2,4-triazole;

3,5-dibutyl-1-[(2'-[(4-hydroxy-2(5H)-furanone-5(Z)-
ylidene)methyl]biphenyl-4-yl]methyl-1H-1,2,4-
triazole;

5-butyl-3-(1,1-difluoropropyl)-1-[(2'-[(4-hydroxy-2(5H)-
furanone-5(Z)-ylidene)methyl]biphenyl-4-yl]methyl-
1H-1,2,4-triazole;

5-butyl-3-phenyl-1-(2'-[(4-hydroxy-2(5H)-furanone-5
(Z)-ylidene)methyl]biphenyl-4-yl]methyl-1H-1,2,4-
triazole;

5-butyl-3-(2-phenylethyl)-1-[2'-[(4-hydroxy-2(5H)-
furanone-5(Z)-ylidene)methyl]biphenyl-4-yl]methyl-
1H-1,2,4-triazole;

5-butyl-3-(4-fluorophenyl)-1-[2'-[(4-hydroxy-2(5H)-
furanone-5(Z)-ylidene)methyl]biphenyl-4-yl]methyl-
1H-1,2,4-triazole;

5-butyl-3-(2-fluorophenyl)-1-[2'-[(4-hydroxy-2(5H)-
furanone-5(Z)-ylidene)methyl]biphenyl-4-yl]methyl-
1H-1,2,4-triazole;

5-butyl-3-(4-pyridyl)-1-[2'-[(4-hydroxy-2(5H)-furanone-
5(Z)-ylidene)methyl]biphenyl-4-yl]methyl-1H-1,2,4-
triazole;

5-butyl-3-(2-furyl)-1-[2'-[(4-hydroxy-2(5H)-furanone-5
(Z)-ylidene)methyl]biphenyl-4-yl]methyl-1H-1,2,4-
triazole;

5-butyl-3-(thiophene-2-yl)-1-[2'-[(4-hydroxy-2(5H)-
furanone-5(Z)-ylidene)methyl]biphenyl-4-yl]methyl-
1H-1,2,4-triazole.

As the specific compounds belonging to the above formula (I-d), the following group of compounds can be mentioned:

1-[2'-[(4-hydroxy-2(5H)-furanone-5(Z)-ylidene)methyl]
biphenyl-4-yl]methyl-4H-1,2,4-triazole;

3,5-dipropyl-1-[2'-[(4-hydroxy-2(5H)-furanone-5(Z)
-ylidene)methyl]biphenyl-4-yl]methyl-4H-1,2,4-
triazole;

3,5-diisopropyl-1-[2'-[(4-hydroxy-2(5H)-furanone-5(Z)-
ylidene)methyl]biphenyl-4-yl]methyl-4H-1,2,4-
triazole;

5-butyl-3-cyclopropyl-1-[2'-[(4-hydroxy-2(5H)-
furanone-5(Z)-ylidene)methyl]biphenyl-4-yl]methyl-
4H-1,2,4-triazole;

3,5-dibutyl-1-[2'-[(4-hydroxy-2(5H)-furanone-5(Z)-
ylidene)methyl]biphenyl-4-yl]methyl-4H-1,2,4-
triazole;

5-butyl-3-(1,1-difluoropropyl)-1-[2'-[(4-hydroxy-2(5H)-furanone-5(Z)-ylidene)methyl]biphenyl-4-yl]methyl-4H-1,2,4-triazole;

5-butyl-3-phenyl-1-[2'-[(4-hydroxy-2(5H)-furanone-5(Z)-ylidene)methyl]biphenyl-4-yl]methyl-4H-1,2,4-triazole;

5-butyl-3-(2-phenylethyl)-1-[2'-[(4-hydroxy-2 (5H)-furanone-5(Z)-ylidene)methyl]biphenyl-4-yl]methyl-4H-1,2,4-triazole;

5-butyl-3-(4-fluorophenyl)-1-[2'-[(4-hydroxy-2(5H)-furanone-5(Z)-ylidene)methyl]biphenyl-4-yl]methyl-4H-1,2,4-triazole;

5-butyl-3-(2-fluorophenyl)-1-[2'-(4-hydroxy-2(5H)-furanone-5(Z)-ylidene)methyl]biphenyl-4-yl]methyl-4H-1,2,4-triazole;

5-butyl-3-(4-pyridyl)-1-[2'-[(4-hydroxy-2(5H)-furanone-5(Z)-ylidene)methyl]biphenyl-4-yl]methyl-4H-1,2,4-triazole;

5-butyl-3-(2-furyl)-1-[2'-[(4-hydroxy-2(5H)-furanone-5(Z)-ylidene)methyl]biphenyl-4-yl]methyl-4H-1,2,4-triazole;

5-butyl-3-(thiophene-2-yl)-1-[2'-[(4-hydroxy-2(5H)-furanone-5(Z) -ylidene)methyl]biphenyl-4-yl]methyl-4H-1,2,4-triazole.

The above compounds according to the present invention can be formed by a conventional method into a salt with a physiologically acceptable acid or base; for example, a salt with an inorganic acid such as hydrochloride, sulfate, or nitrate; a salt with an organic acid such as acetate, oxalate, succinate, or maleate a salt with an alkali metal such as sodium salt or potassium salt; or a salt with an alkali earth metal such as a calcium salt.

GENERAL SYNTHESIS PROCESS

The compounds according to this invention can be synthesized, for example, according to the following process of the schemes I and II. In the following description, numbers 1 to 19 attached to the compounds correspond respectively to each compound in the schemes I and II that bears that number. In addition, references (a) to (k) attached to the compounds correspond respectively to compounds bearing these references, the substituents $R^1$ and $R^2$ of which are shown below.

|   | $R^1$ | $R^2$ |
|---|---|---|
| a | n-$C_3H_7$ | n-$C_3H_7$ |
| b | iso-$C_3H_7$ | iso-$C_3H_7$ |
| c | Cyclopropyl | n-$C_4H_9$ |
| d | n-$C_4H_9$ | n-$C_4H_9$ |
| e | Phenyl | n-$C_4H_9$ |
| f | 2-Phenylethyl | n-$C_4H_9$ |
| g | 4-Fluorophenyl | n-$C_4H_9$ |
| h | 2-Fluorophenyl | n-$C_4H_9$ |
| i | Pyridine-4-yl | n-$C_4H_9$ |
| j | Furan-2-yl | n-$C_4H_9$ |
| k | Thiophene-2-yl | n-$C_4H_9$ |

Scheme 1

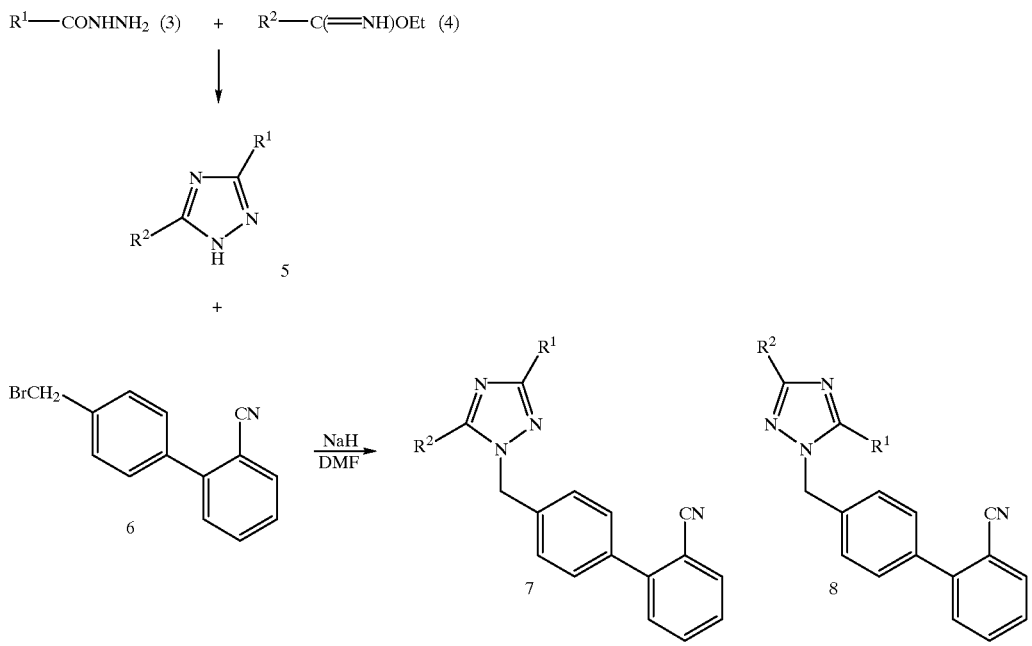

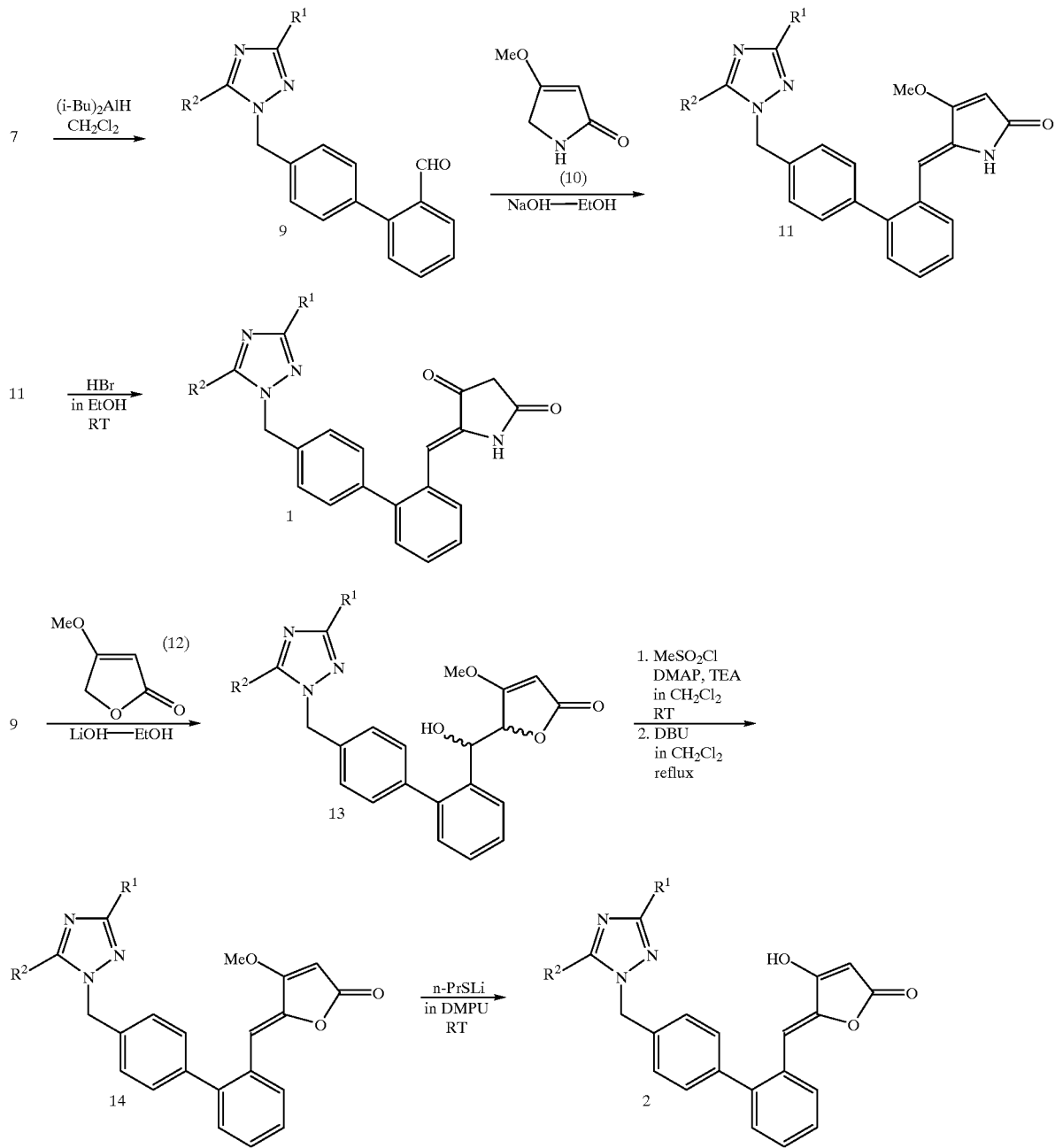

As shown in Scheme 1, the compounds according to this invention (compounds 1 and 2) can be synthesized using a pathway starting with the alkylation of 3,5-di-substituted-1H-1,2,4-triazole (compound 5) and 4-bromomethyl-2'-cyanobiphenyl (compound 6). Symmetrical and asymmetrical triazoles (compounds 5a to 5k) can be obtained at a high yield by heating acylhydrazone (compound 3) and ethyliminocarboxylate (compound 4). Compounds 5a to 5k were reacted with compound 6 in N,N-dimethylformamide (DMF) in the presence of NaH at room temperature to obtain compound 7. The asymmetrical triazoles (compounds 5c, 5e to 5h, 5j, and 5k) also provide position isomers (compound 8). Most of the position isomers can be mutually separated using silica gel column chromatography, and the configuration of each isomer was determined based on the fact that the main product was generally compound 7 and based an two-dimensional nuclear Overhauser effect spectra (NOESY). The isomers that could not be separated were used for the subsequent reaction in the form of mixtures.

Compound 7 was reacted with diisobutyl aluminum hydride to obtain the corresponding compound 9, which was used as an intermediate common to target compounds 1 and 2.

An ethanol solution of compound 9 and 4-methoxyl-2-pyrrolidone (compound 10) was treated with alkali to obtain compound 11. The configuration of compound 11 was determined based on the NOE between OMe and 5-ylidene H in $^1$H-NMR spectra. Finally, compound 11 was O-demethylated using HBr to obtain target compound 1 having a (Z)-5-ylidene structure.

Tetronic-acid-like compound 2 of compound 1 was obtained by reacting compound 9 with 4-methoxy-2-furanone (compound 12). However, in contrast to the reaction with the above pyrrolidone (compound 10), by the reaction between the compounds 9 and 12, an aldol reaction product (compound 13) was obtained. This compound was O-mesylated and subsequently treated with 1,8-diazabicyclo [5,4,0]-undec-7-ene (DBU) for dehydration. In most cases, this reaction resulted in a mixture of compound 14 and its (E)-isomer, but its stereoselectivity was very high (>90:10). Compound 14 and its (E)-isomer were O-demethylated by reacting lithium-2-propanethiolate in N,N'-dimethylpropylene urea (DMPU) at room temperature to obtain the same (Z)-5-ylidenetetronic acid (compound 2). It has been determined from IR and $^1$H-NMR spectrum data that compound 2 has a 4-hydroxyfuranone structure, which is shown in Scheme 1, instead of a 2,4-dioxo structure, which is a tautomer.

Since a distinct angiotensin II receptor antagonism was observed in compounds 1d and 2d, the present 4H-1,2,4-triazole compounds 19a and 19b also were synthesized in accordance with the following scheme. The key intermediate 1-(2'-cyanobiphenyl-4-methyl) triazole (compound 17) was obtained by condensing acylhydrazone (compound 15) and 4-aminomethyl-2'-cyanobiphenyl (compound 16). Intended compounds 19a and 19b were derived from compound 17 using the above method for deriving compounds 1 and 2 from compound 7.

II receptor antagonistic compound and medically acceptable carrier and/or diluent, wherein the angiotensin II receptor antagonistic compound is selected from the compound of the formula (I) or its medically acceptable salts.

Specifically, this invention relates to a therapeutic agent for circulatory system disease such as hypertension and heart failure containing the compound of the formula (I) and its medically acceptable salts.

When using the present compound as a medicine, the present compound is orally or parenterally administered. The dosage depends on the disease, the symptoms, the recipient, and the administration method, but if the compound is administered as a medicine for adult essential hypertension, administration is preferably carried out once to three times a day so that the total amount of administered medicine is about 1 to 1,000 mg for oral administration, while it is normally 0.1 to 100 mg/kg for injections.

If such a medicine can be prepared in the form of an oral formulation, an appropriate pharmacologically acceptable excipient and a carrier are added to the main component to produce tablets, powder, granules, or capsules according to conventional methods. The carriers that can be used in this invention include lactose, sucrose, corn starch, glucose, celluloses, cellulose esters, starch powders, dextrin, pectin, gelatin, gum arabic, polyethyleneglycol, silicon dioxide, talc, silica gel, sodium alginate, sodium citrate, sodium stearate, magnesium oxide, sodium phosphate, sodium sulfate, polyvinylpyrrolidone, polyvinylalcohol, and propy- Scheme 2

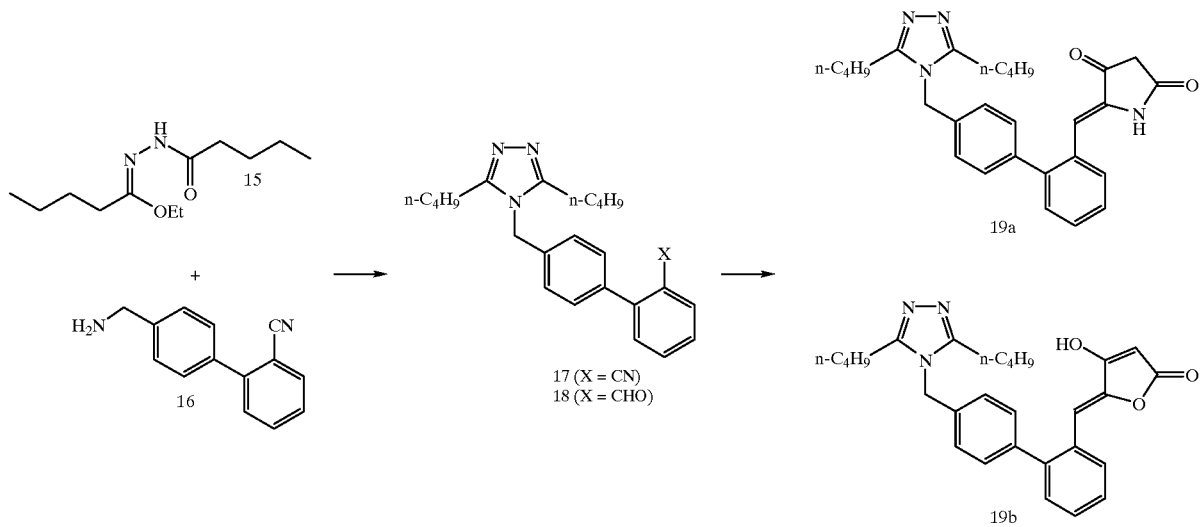

Toxicities of the present compounds are low a safety of them is high. Based on the angiotensin II antagonism, they strongly suppress the vascular contraction and hypertensive effects by angiotensin II, thereby reducing the blood pressure of animals, in particular, mammals such as humans, dogs, monkeys, rabbits, and rats. Thus, the present compounds are effective as therapeutic agents for hypertension and other diseases based on angiotensin II, specifically, for hypertension such as essential, renal, or renovascular hypertension and circulatory system diseases including heart failure.

Thus, this invention relates to a medical composition containing a therapeutically effective amount of angiotensin leneglycol. Furthermore, cocoa powder, peppermint oil, aromatic acid, or cinnamon powder may be used as required. In addition, hydroxypropylmethylcellulose can be used as a control release component.

If an injection is prepared as a parenteral formulation, the above carrier and a diluent or solvent agent can be added to the main component as required to obtain an intravenous, subcutaneous, or intramuscular injection using a normal method. The diluent and solvents that can be used in this invention include water, ethanol, corn oil, cotton seed oil, peanut oil, sesame oil, benzylalcohol, brine and/or various buffer, Polysolvate 80, polyoxyethylenesorbitanmonolaurate, and macrogol.

Moreover, sodium sulfite, parahyroxybenzoic acid and its esters, or sorbic acid can be added as a stabilizer.

BEST MODE FOR CARRYING OUT THE INVENTION

This invention is illustrated in detail by reference examples, examples, test examples, and formulation examples, but of course, these do not limit this invention.

In the following examples, the melting point was measured using a Yanagimoto micro melting-point measuring apparatus, and all melting point values are uncorrected. The boiling point was measured by a Kugelrohr distilling apparatus. $^1$H-NMR spectra were measured by a Varian Gemini-300, Varian Unity plus-500 nuclear magnetic resonance apparatus, and Me$_4$Si or CHCl$_3$ ($\delta$7.26) was used as an internal standard. The following abbreviation are used for signal division forms. s=singlet, d=doublet, t=triplet, q=quartet, m=multiplet, br=broad. Electron impact mass spectrometry (EI-MS) and high-resolution mass spectrometry (HR-MS) were performed using a Jeol JMS-AX505HAD. IR spectra were measured using a PERKIN ELMER 1,600 Fourier transform (FT) infrared spectroscopic analyzer. Column chromatography was carried out using Fuji-Davison BW-200 silica gel (150–325 mesh) and E. Merk 9385 silica gel 60 (230–400 mesh). The 1% KH$_2$PO$_4$-treated silica gel was obtained by immersing E. Metk 9385 silica gel 60 (230–400 mesh) in a 1% KH$_2$PO$_4$ water solution and drying the solution. The analysis TLC plate was coated with E. Mark silica gel 60F-254 (0.25 mm). Acylhydrazine (compound 3) was obtained by reacting ester with hydrazine, and ethyliminocarboxylate (compound4) was obtained from a hydrochloride of compound 4, which was obtained by reacting nitrile with dry HCl in ethylalcohol.

REFERENCE EXAMPLE 1

Synthesis of the Intermediate Compound 5d: 3,5-Dibutyl-1H-1,2,4-triazole

Under a nitrogen atmosphere, compound 3d (4.00 g, 34.5 mmol) was added to an absolute ethanol solution (50 ml) of compound 4d (4.45 g; 34.5 mmol) and the mixture was heated and refluxed. Then, 5 hours later, 4.45 g (34.5 mmol) of compound 4d was added to the mixture, and 25 hours later 1.12 g (8.7 mmol) of compound 4d was added, and the mixture was heated for 28 hours. After this heat reaction, the reaction liquid was condensed under reduced pressure, and the residue was subjected to column chromatography (silica gel 90 g: hexane/ethyl acetate=3:2) to obtain white solid 5d (5.53 g; yield: 85%).

b.p.112–115° C./0.45 Torr, m.p.42–43° C. (lit. 50.5 to 51.5° C.) (after recrystallization from hexane/iso-Pr$_2$O), Rf=0.35 (hexane/ethyl acetate=1:2), $^1$H-NMR (300 MHz, CDCl$_3$) $\delta$:0.91 (6H, t, J=7.6 Hz, Me), 1.37 (4H, qt, J=7.6Hz, CH$_2$Me), 1.71 (4H, tt, J=7.6 Hz, CH$_2$Et), 2.73 (4H, t, J=7.6 Hz, CH$_2$Pr); Elementary analysis: C$_{10}$H$_{15}$N$_3$; Calculated: C: 66.26, H: 10.56, N: 23.18; Found: C: 66.38, H: 10.68, N: 23.24.

Other 1H-1,2,4-triazole compounds 5a, 5b, 5c, 5e, 5f, 5g, 5h, 5i, 5j, and 5k were obtained in the same manner as described above. Their yields and physical property values are shown below.

Compound 5a: 3,5-Dipropyl-1H-1,2,4-triazole

Yield: 91%, b.p.103–106° C./0.47 Torr, m,p.62° C. (lit. 69 to 70° C.), $^1$H-NMR (300 MHz, CDCl$_3$) $\delta$: 0.96 (6H, t, J=7.5 Hz, Me), 1.76 (4H, qt, J=7.5 Hz, CH$_2$Me), 2.71 (4H, t, J=7.5 Hz, CH$_2$Et); Elementary analysis: C$_8$H$_{15}$N$_3$; Calculated: C: 62.71, H; 9.87, N: 27.42; Found: C: 62.67, H: 9.97, N: 27.72.

Compound 5b: 3,5-Diisopropyl-1H-1,2,4-triazole

Yield: 82%, colorless needle like crystals from iso-Pr$_2$O, m.p.140° C., $^1$H-NMR (300 MHz, CDCl$_3$) $\delta$: 1.33 (12H, d, J=7.1 Hz, Me), 3.08 (2H, qq, J=7.1 Hz, CH$_2$Me); Elementary analysis: C$_8$H$_{15}$N$_3$; Calculated: C: 62.71, H: 9.87, N: 27.42; Found: C; 62.82, H: 9.90, N: 27.55.

Compound 5c: 5-Butyl-3-cyclopropyl-1H-1,2,4-triazole

Yield: 80%, colorless needle like crystals from iso-Pr$_2$O, m.p.65° C., $^1$H-NMR (300 MHz, CDCl$_3$) $\delta$: 0.87 (3H, t, J=7.1 Hz, Me), 0.90 to 0.99 (4H, m, cyclopropanCH$_2$), 1.34 (2H, qt, J=7.1 Hz, CH$_2$Me), 1.66 (2H, tt, J=7.1 Hz, CH$_2$Et), 1.98 (1H, m, cyclopropyl-H), 2.60 (2H, t, J=7.1 Hz, CH$_2$Pr); Elementary analysis: C$_9$H$_{15}$N$_3$; Calculated: C: 65.42, H: 9.15, N: 25.43; Found: C: 65.25, H: 9.07, N: 25.35.

Compound 5e: 5-Butyl-3-phenyl-1H-1,2,4-triazole

Yield: 52%, colorless needle like crystals from iso-Pr$_2$O, m.p.85 to 86° C., $^1$H-NMR (300 MHz, CDCl$_3$) $\delta$: 0.86 (3H, t, J=7.5 Hz, Me), 1.31 (2H, qt, J=7.5 Hz, CH$_2$Me), 1.69 (2H, tt, J=7.5 Hz, CH$_2$Et), 2.75 (2H, t, J=7.5 Hz, CH$_2$Pr), 7.3 to 7.40 (3H, m, ArH), 7.99 to 8.02 (2H, m, ArH); Elementary analysis; C$_{12}$H$_{15}$N$_3$; Calculated, C: 71.61, H: 71.51, N: 20.88; Found: C: 71.56, H: 7.46, N: 21.18.

Compound 5f: 5-Butyl-3-(2-phenylethyl)-1H-1,2,4-triazole

Yield: 97%, b.p.141 to 144° C./0.47 Torr, m.p.58 to 60° C., $^1$H-NMP. (300 MHz, CDCl$_3$) $\delta$: 0.93 (3H, to J=7.5 Hz, Me), 1.38 (2H, qt, J=7.5 Hz, CH$_2$Me), 1.73 (2H, tt, J=7.5 Hz, CH$_2$Et), 2.75 (2H, t, J=7.5 Hz, CH$_2$Pr), 3.05 (4H, s, phenylethyl), 7.17 to 7.30 (5H, m, ArH); Elementary analysis: C$_{14}$H$_{19}$N$_3$; Calculated: C: 73.3, H: 8.35, N: 18.32; Found: C: 73.27, H: 8.43, N: 18.54.

Compound 5g: 5-Butyl-3-(4-fluorophenyl)-1H-1,2,4-triazole

Yield: 68%, colorless needle like crystals from iso-Pr$_2$O, m.p.93 to 94° C., $^1$H-NMR (300 MHz, CDCl$_3$) $\delta$: 0.92 (3H, t, J=7.6 Hz, Me), 1.39 (2H, qt, J=7.6 Hz, CH$_2$Me), 1.75 (2H, tt, J=7.6Hz, CH$_2$Et), 2.81 (2H, t, J=7.6 Hz, CH$_2$Pr), 7.11 (2H, t, J=8.8 Hz, ArH), 8.02 (2H, dd, j=8.8, 5.5 Hz, ArH); Elementary analysis: C$_{12}$H$_{14}$N$_3$F: Calculated: C: 65.74, H: 6.44, N: 19.16; Found: C: 65.84, H: 6.48, N: 19.39.

Compound 5h: 5-Butyl-3-(2-fluorophenyl)-1H-1,2,4-triazole

Yield: 79%, colorless oil, b.p.208 to 210° C./0.9 Torr, $^1$H-NMR (300 MHz, CDCl$_3$) $\delta$: 0.94 (3H, t, J=7.6 Hz, Me), 1.42 (2H, qt, J=7.6 Hz, CH$_2$Me), 1.78 (2H, tt, J=7.6 Hz, CH$_2$Et), 2.83 (2H, t, J=7.6 Hz, CH$_2$Pr), 7.19 (1H, t, J=7.7 Hz, ArH), 7.25 (1H, d, J=7.7 Hz, ArH), 7.41 (1H, t, J=7.7 Hz, ArH), 8.19 (1H, t, J7.7 Hz, ArH); Elementary analysis: C$_{12}$H$_{14}$N$_3$F: Calculated: C: 65.74, H: 6.44, N: 19.16; Found: C; 65.64, H: 6.47, N: 19.45.

Compound 5i: 5-Butyl-3-(pyridine-4-yl)-1H-1,2,4-triazole

Yield: 55%, colorless needle like crystals from iso-Pr$_2$O, m.p.108 to 109° C., $^1$H-NMR (300 MHz, CDCl$_3$) $\delta$: 0.94

(3H, t, J=7.6 Hz, Me), 1.42 (2H, qt, J=7.6 Hz, CH$_2$Me), 1.80 (2H, tt, J=7.6Hz, CH$_2$Et), 2.89 (2H, t, J=7.6 Hz, CH$_2$Pr), 8.03 (2H, dd, J=4.5, 1.7 Hz, ArH), 8.71 (2H, dd, J=4.5, 1.7 Hz, ArH), 13.00 (1H, brs. NH); Elementary analysis: C$_{11}$H$_{14}$N$_4$; Calculated: C: 65.32, H: 6.98, N: 27.70; Found: C: 65.03, H: 6.84, N: 27.91.

Compound 5j: 5-Butyl-3-(furan-2-yl)-1H-1,2,4-triazole

Yield: 95%, plate like crystals from AcOEt, m.p.73 to 74° C. $^1$H-NMR (300 MHz, CDCl$_3$) δ: 0.91 (3H, t, J=7.6 Hz, Me), 1.38 (2H, qt, J=7.6 Hz, CH$_2$Me), 1.76 (2H, tt, J=7.6Hz, CH$_2$Et), 2.83 (2H, t, J=7.6 Hz, CH$_2$Pr), 6.51 (1H, dd, J=3.4, 1.7 Hz, ArH), 6.99 (1H, dd, J=3.4, 0.6 Hz, ArH), 7.49 (1H, dd, J=1.7, 0.6 Hz, ArH); Elementary analysis: C$_{10}$H$_{13}$N$_3$O; Calculated: C: 62.81, H: 6.85, N: 21.97; Found: C: 63.01, H: 6.87, N: 22.26.

Compound 5k: 5-Butyl-3-(thiophene-2-yl)-1H-1,2,4-triazole

Yield: 74%, plate like crystals from iso-Pr$_2$O, m.p. 60 to 61° C., $^1$H-NMR (300 MHz, CDCl$_3$) δ: 0.90 (3H, t, J=7.6 Hz, Me), 1.37 (2H, qt, J=7.6 Hz, CH$_2$Me), 1.73 (2H, tt, J=7.6 Hz, CH$_2$Et), 2.79 (2H, t, J=7.6 Hz, CH$_2$Pr), 7.08 (1H, dd, J=5.1, 3.7 Hz, ArH), 7.34 (1H, dd, J=5.1, 1.1 Hz, ArH), 7.64 (1H, dd, J=3.7, 1.1 Hz, ArH); Elementary analysis: C$_{10}$H$_{13}$N$_3$S: Calculated; C: 57.94, H: 6.32, N: 20.27; Found: C: 57.83, H: 6.42, N: 20.38.

REFERENCE EXAMPLE 2

Synthesis of the Intermediate Compound 7d: 3,5-dibutyl-1-(2'-cyanobiphenyl-4-yl)methyl-1H-1,2,4-triazole NaH (60%) (96 mg, 2.4 mmol) was added to anhydrous DMF (5 ml) in a nitrogen atmosphere, and anhydrous DMF (4 ml) solution of compound 5d (0.43 g, 2 mmol) was added dropwise to the mixture, which was being cooled in an ice water bath. Twenty minutes later, a anhydrous DMF (4 ml) solution of 4-bromomethyl-2'-cyanobiphenyl (compound 6) (0.82 g, 3 mmol) was added to the mixture, and the ice water bath was removed. The mixture was stirred at room temperature for 2 hours, and saturated aqueous NH$_4$Cl solution (10 ml) was added to the reaction liquid, followed by Et$_2$O extraction. (60 ml×2). The organic phase was washed with saturated brine (30 ml×2), and dried over magnesium sulfate. And then, the phase was condensed under reduced pressure. The residue was subjected to column chromatography (silica gel, 47 g, hexane/ethyl acetate=1:1) to obtain colorless oily substance 7d (0.63 g, 85%).

Rf=0.47 (hexane/ethyl acetate=1:1), IR (neat): 2224 cm$^{-1}$, $^1$H-NMR (500 MHz, CDCl$_3$) δ: 0.89, 0.93 (each 3H, t, J=7.6 Hz, Me), 1.35, 1.39 (each 2H, qt, J=7.6 Hz, CH$_2$Et), 1.67, 1.73 (each 2H, tt, J=7.6 Hz, CH$_2$Et), 2.96, 2.70 (each 2H, t, J=7.6 Hz, CH$_2$Pr), 5.30 (2H, s, N$_1$—CH$_2$), 7.24 (2H, d, J=8.4 Hz, ArH-3, 5),7,44 (1H, td, J=7.7 Hz, ArH-4'), 7.47 (1H, ddd, J=7.7, 1.2, 0.5 Hz, ArH-6'), 7.53 (2H, d, J=8.4, ArH-2, 6), 7.64 (1H, td, J=7.7, 1.4 Hz, ArH-5'), 7.76 (1H, ddd, J=7.7, 1.4, 0.5 Hz, ArH-3'), MSm/z372 (M$^+$), 343, 329, 192 (base peak); Elementary analysis: C$_{24}$H$_{28}$N$_4$; Calculated: C: 77.38, H: 7.58, N: 15.04; Found: C: 77.12, H: 7.55, N: 14.92.

Other 1-(2'-cyanobiphenyl-4-yl)methyl-1H-1,2,4-triazole compounds 7a, 7b, 7c, 7e, 7f, 7g, 7h, 7i, 7j and 7k were obtained in the same manner as described above. Their yields and physical property values are shown below. For position isomers 8c and 8e to 8k, $^1$H-NMR spectra showed that the peak of CH$_2$Pr moved to low magnetic fields (<0.44 ppm).

Compound 7a: 3,5-Dipropyl-1-(2'-cyanobiphenyl-4-yl)methyl-1H-1,2,4-triazole

Yield: 94%, oil, elementary analysis: C$_{22}$H$_{24}$N$_4$: Calculated: C: 76.71, H: 7.02, N: 16.27; Found: C: 76.76, H: 7.06, N: 16.23.

Compound 7b: 3,5-Diisopropyl-1-(2'-cyanobiphenyl-4-yl)methyl-1H-1,2,4-triazole

Yield: 99%, needle like crystals obtained by recrystallization from iso-Pr$_2$O, m.p.71 to 72° C., elementary analysis: C$_{22}$H$_{24}$N$_4$: Calculated: C: 76.71, H: 7.02, N: 16.27; Found: C: 76.62, H: 7.25, N: 16.13.

Compound 7c: 5-Butyl-3-cyclopropyl-1-(2'-cyanobiphenyl-4-yl)methyl-1H-1,2,4-triazole Yield: 49% (ratio of isomers to compound 7c/compound 8c=60:40), oil, elementary analysis: C$_{23}$H$_{24}$N$_4$: Calculated: C: 77.50, H: 6.79, N: 15.72; Found: C: 77.25, H: 6.82, N: 15.74.

Compound 7e: 5-Butyl-3-phenyl-1-(2'-cyanobiphenyl-4-yl)methyl-1H-1,2,4-triazole

Yield: 58% (ratio of isomers to compound 7e/compound 8e=78:22), needle like crystals obtained by recrystallization from iso-Pr$_2$O, m.p.74 to 75° C., elementary analysis; C$_{26}$H$_{24}$N$_4$: Calculated: C: 79.56, H: 6.16, N: 14.27: Found: C: 79.28, H: 6.12, N: 14.42.

Compound 7f: 5-Butyl-3-(2-phenylethyl)-1-(2'-cyanobiphenyl-4-yl)methyl-1H-1,2,4-triazole Yield: 52% (ratio of isomers to compound 7f/compound 8f=53:46), oil, elementary analysis; C$_{28}$H$_{28}$N$_4$: Calculated: C: 79.97, H: 6.71, N: 13.32; Found: C: 79.98, H: 6.72, N: 13.09.

Compound 7g: 5-Butyl-3-(4-fluorophenyl)-1-(2'-cyanobiphenyl-4-yl)methyl-1H-1,2,4-triazole Yield: 91% (ratio of isomers to compound 7g/compound 8g=92:8), needle like crystals obtained by recrystallization from iso-Pr$_2$O, m.p.109 to 110° C., elementary analysis: C$_{26}$H$_{23}$N$_4$F: Calculated; C: 76.08, H: 5.65, N: 13.65; Found: C: 75.87, H: 5.47, N: 13.35.

Compound 7h: 5-Butyl-3-(2-fluorophenyl)-1-(2'-cyanobiphenyl-4-yl)methyl-1H-1,2,4-triazole Yield: 69% (ratio of isomers to compound 7h/compound 8h=89:11), needle like crystals obtained by recrystallization from iso-Pr$_2$O, m.p.81° C., elementary analysis: C$_{26}$H$_{23}$N$_4$F: Calculated: C: 76.08, H: 5.65, N: 13.65; Found: C: 76.00, H: 5.48, N: 13.39.

Compound 7i: 5-Butyl-3-(pyridine-4-yl)-1-(2'-cyanobiphenyl-4-yl)methyl-1H-1,2,4-triazole Yield: 46%, needle like crystals obtained by recrystallization from iso-Pr$_2$O, m.p.138 to 139° C., elementary analysis: C$_{25}$H$_{23}$N$_3$: Calculated: C: 76.31, H: 5.89, N: 17.80; Found: C: 76.08, H: 5.83, N: 17.74.

Compound 7j: 5-Butyl-3-(furan-2-yl)-1-(2'-cyanobiphenyl-4-yl)methyl-1H-1,2,4-triazole Yield: 62% (ratio of isomers to compound 7j/compound 8j=70:30), plate like crystals obtained by recrystallization from iso-Pr$_2$O, m.p.77.5 to 78.5° C., elementary analysis: C$_{24}$H$_{22}$N$_4$O: Calculated: C: 75.37, H: 5.80, N: 14.65; Found: C: 75.35, H: 5.59, N: 14.72.

Compound 7k: 5-Butyl-3-(thiophene-2-yl)-1-(2'-cyanobiphenyl-4-yl)methyl-1H-1,2,4-triazole Yield: 86% (ratio of isomers to compound 7k/compound 8k=88:12), needle like crystals obtained by recrystallization from iso-Pr$_2$O, m.p.73 to 74° C., elementary analysis: C$_{24}$H$_{22}$N$_4$S: Calculated: C: 72.33, H: 5.56, N: 14.06; Found: C: 72.09, H: 5.32, N: 14.06.

REFERENCE EXAMPLE 3

Synthesis of the Intermediate Compound 9d: 3,5-Dibutyl-(2'-formylbiphenyl-4-yl)methyl-1H-1,2,4-triazole Under a nitrogen atmosphere, compound 7d (4.1 g, 11 mmol) was dissolved in anhydrous CH$_2$Cl$_2$ (80 ml). A 0.98M hexane solution (28 ml, 27 mmol) of iso-Bu$_2$AlH was added dropwise to the mixture, while stirring and cooling at −80° C., and 1 hour later, the reaction liquid was poured into a mixture of acetic acid (20 ml) and ice (20 g), to which 1N HCl (20 ml) was then added. After one hour of stirring, the organic phase was separated and washed with saturated NaHCO$_3$ aqueous solution (50 ml×2) and then with saturated brine (50 ml×1). After drying over magnesium sulfate, the organic phase was condensed under reduced pressure, and the residue was subjected to column chromatography (silica gel, 90 g, hexane/ethyl acetate=1:1) to obtain a colorless oily substance 9d (3.84 g: yield: 93%).

Rf=0.47 (hexane/ethyl acetate=1:1), IR (neat): 1773, 1745 cm$^{-1}$, $^1$H-NMR (500 MHz, CDCl$_3$) δ: 0.90, 0.94 (each 3H, t, J=7.6 Hz, Me), 1.36, 1.40 (each 2H, qt, J=7.6 Hz, CH$_2$Me), 1.67, 1.74 (each 2H, tt, J=7.6 Hz, CH$_2$Et), 2.69, 2.71 (each 2H, t, J=7.6 Hz, CH$_2$Pr), 5.32 (2H, s, N$_1$—CH$_2$), 7.23 (2H, d, J=8.4Hz, ArH-3, 5), 7.36 (2H, d, J=8.3 Hz, ArH-2, 6), 7.41 (1H, d, J=7.9 Hz, ArH-6'), 7.51 (1H, dd, J=7.6, 7.5 Hz, ArH-4'), 7.64 (1H, dd, J=7.9, 7.5 Hz, ArH-5'), 8.02 (1H, d, J=7.6 Hz, ArH-3'), 9.95 (1H, s, CHO), EI-MSm/z; 375 (M$^+$), 346, 333 (base peak), 195, 167, 165, HR-MSm/z; Calculated: C$_{24}$H$_{28}$N$_3$O (M$^+$); 375, 2311; Found: 375, 2306.

Other 1-(2'-formylbiphenyl-4-yl)methyl-1H-1,2,4-triazole compounds 9a to 9c and 9e to 9k were obtained from corresponding nitrile compounds using a reduction method similar to that described above, and were then subjected to silica gel column chromatography for the next reaction.

EXAMPLE 1

Synthesis of the Present Compound 1d: 3,5-Dibutyl-1-[2'-[(2,4-dioxopyrrolidine-5(Z)-ylidene)methyl]biphenyl-4-yl]methyl-1H-1,2,4-triazole Compound 9d (405 mg, 1.08 mmol) and 4-methoxy-2(5H)-pyrrolidone (compound 10) (305 mg, 2.70 mmol) were dissolved in absolute ethanol (0.5 ml), and 1N sodium hydroxide (4 ml) was added to the mixture. After 1 hour of stirring at room temperature, the reaction liquid was diluted with ethyl acetate (20 ml). After washing with water (10 ml), the liquid was dried over magnesium sulfate and was condensed under reduced pressure. The residue was subjected to column chromatography (silica gel, 47 g, hexane/ethyl acetate=1:3) to obtain a colorless oily substance (compound 11d). The physical property values of compound 11d are shown below.

Rf=0.24 (hexane/ethyl acetate=1:3), IR (neat): 3649, 1684 cm$^{-1}$, $^1$H-NMR (500 MHz, CDCl$_3$) δ: 0.88, 0.93 (each 3H, t, J=7.4 Hz, Me), 1.34, 1.40 (each 2H, qt, J=7.4 Hz, CH$_2$Me), 1.67, 1.73 (each 2H, tt, J=7.4 Hz, CH$_2$Et), 2.67, 2.70 (each 2H, t, J=7.4 Hz, CH$_2$Pr), 3.81 (3H, s, OMe), 5.16 (1H, sH-3"), 5.30 (2H, s, N$_1$—CH$_2$), 6.13 (1H, s, 5"=CH), 7.16 (2H, d, J=8.0 Hz, ArH-3, 5), 7.31 (2H, d, J=8.0 Hz, ArH-2, 6) 7.34–7.41 (3H, m, ArH-4', 5', 6') 7.51 (1H, d, J=7.3 Hz, ArH-3').

Compound 11d (0.95 g, 2.02 mmol) was dissolved in methanol (7 ml), and 47% HBr (10 ml) was added to the mixture. After 1 about of stirring at room temperature, the reaction liquid was condensed under reduced pressure. CHCl$_3$ (40 ml×3) was added to the residue for extraction, and the organic phase was washed with water (40 ml). After drying over sodium sulfate, the phase was condensed under reduced pressure, and the residue was subjected to column chromatography (1% KH$_2$PO$_4$-treated silica gel, 41 g, hexane/ethyl acetate=1:3) to obtain compound 1d (0.21 g, 23%), which was a crystalline solid. The compound was recrystallized from ethyl acetate to obtain colorless sandlike crystals with m.p.179 to 180° C.

Rf=0.19 (hexane/ethyl acetate=1:2), IR (KBr): 3437, 1674, 1587 cm$^{-1}$; (CHCl$_3$): 1758, 1726, 1645 cm$^{-1}$, $^1$H-NMR (500 MHz, CDCl$_3$; δ: 0.99, 0.94 (each 3H, t, J=7.5 Hz, Me), 1.37, 1.40 (each 2H, qt, J=7.5 Hz, CH$_2$Me), 1.69, 1.73 (each 2H, tt, J=7.5 Hz, CH$_2$Et), 2.69, 2.70 (each 2H, t, J=7.5 Hz, CH$_2$Pr), 3.13 (2H, s, CH$_2$-3"), 5.29 (2H, s, N$_1$—CH$_2$), 6.43 (1H, s, 5"=CH), 7.17 (2H, d, J=8.1 Hz, ArH-3, 5), 7.30 (2H, d, J=8.1 Hz, ArH-2, 6), 7.39–7.45 (4H, m, ArH-3', 4', 5', 6'), 8.01 (1H, or NH).

Elementary analysis, C$_{28}$H$_{32}$N$_4$O$_2$; Calculated. C: 73.66, H: 7.06, N: 12.27; Found: C: 73.51, H: 7.05, N: 12.30.

Other 1-[2'-[(2,4-dioxopyrrolidine-5(Z)-ylidene)methyl]biphenyl-4-yl]methyl-1H-1,2,4-triazole compounds 1a, 1b, 1a, 1e, 1f, 1g, 1h, 1i, 1j, and 1k were obtained in the same manner as described above. Their yields and physical property values are shown below.

Compound 1a: 3,5-Dipropyl-1-[2'-[(2,4-dioxopyrrolidine-5(Z)-ylidene)methyl]biphenyl-4-yl]methyl-1H-1,2,4-triazole Yield 24% (from compound 9), m.p.179 to 180° C., plate like crystals (from ethanol), elementary analysis: C$_{26}$H$_{28}$N$_4$O$_2$; Calculated: C: 72.87, H: 6.59, N: 13.07, Found: C: 73.14, H: 6.51, N: 13.22; $^1$HNMR (500 MHz, CDCl$_3$) data; 3,5 substituent of triazole: 0.96, 0.98 (each 3H, t, J=7.6 Hz), 1.75, 1.77 (each 2H, qt, J=7.6 Hz), 2.67, 2.68 (each 2H, t, J=7.6 Hz); Biphenyl methyl group: 5.30 (2H, s), 7.17 (2H, d, J=8.2 Hz), 7.29 (2H, d, J=8.2 Hz), 7.37–7.48 (4H, m); Dioxopyrrolidine group: 3.12 (2H, s), 6.43 (1H, s), 8.10 (1H, s).

Compound 1b: 3,5-Diisopropyl-1-[2'-[(2,4-dioxopyrrolidine-5-(Z)-ylidene)methyl]biphenyl-4-yl]methyl-1H-1,2,4-triazole Yield 24% (from compound 9), m.p.141 to 142° C., sand like crystals (from ethyl acetate), elementary analysis: C$_{26}$H$_{28}$N$_4$O$_2$; Calculated: C: 72.87, H: 6.59, N: 13.07, Found: C: 72.70, H: 6.30, N: 12.98; $^1$H-NMR (500 MHz, CDCl$_3$) data; 3,5 substituent of triazole: 1.27, 1.35 (each 6H, d, J=6.9 Hz), 3.01, 3.07 (each 1H, qq, J=6.9 Hz); Biphenyl methyl group: 5.33 (2H, s), 7.15 (2H, d, J=8.2 Hz), 7.29 (2H, d, J=8.2 Hz), 7.37–7.46 (4H, m); Dioxopyrrolidine group: 3.11 (2H, s), 6.42 (1H, s), 8.08 (1H, s).

Compound 1c: 5-Butyl-3-cyclopropyl-1-[2'-[(2,4-dioxopyrrolidine-5(Z)-ylidene)methyl]biphenyl-4-yl]methyl-1H-1,2,4-triazole Yield 23% (from compound 9), m.p.166 to 168° C., plate like crystals (from ethyl acetate), elementary analysis:

$C_{27}H_{28}N_4O_2$; Calculated: C: 73.61, H: 6.41, N: 12.72, Found. C: 73.47, H: 6.33, N; 12.59; $^1$H-NMR (500 MHz, CDCl$_3$) data; 3,5 substituent of triazole: 0.90, 0.98 (7H, m), 1.38 (2H, qt, J=7.5 Hz), 1.62 (tt, J=7.5 Hz), 1.97–2.00 (1H, m), 2.66 (2H, t, J=7.5); Biphenyl methyl group: 5.26 (2H, s), 7.18 (2H, d, J=8.2 Hz), 7.29 (2H, d, J=8.2 Hz), 7.37–7.48 (4H, m); Dioxopyrrolidine group: 3.12 (2H, s), 6.43 (1H, s), 8.10 (1H, s).

Compound 1e: 5-Butyl-3-phenyl-1-[2'-[(2,4-dioxopyrrolidine-5(Z)-ylidene)methyl]biphenyl-4-yl]methyl-1H-1,2,4-triazole Yield 15% (from compound 9), m.p.180 to 181° C., amorphous solid (from ethyl acetate), elementary analysis: $C_{30}H_{28}N_4O_2$; Calculated: C: 75.61, H: 5.92, N: 11.76, Found: C: 75.50, H: 5.75, N: 11.65; $^1$H-NMR (500 MHz, CDCl$_3$) data; 3,5 substituent of triazole: 0.92 (3H, t, J=7.6 Hz), 1.41 (2H, qt, J=7.6 Hz), 1.73 (2H, tt, J=7.6 Hz), 2.77 (2H, t, J=7.6 Hz), 7.37–7.46 (3H, m), 8.11 (2H, d, J=8.2); Biphenyl methyl group: 5.41 (2H, s), 7.24 (2H, d, J=8.2 Hz), 7.30 (2H, d, J=8.2 Hz), 7.37–7.46 (4H, m); Dioxopyrrolidine group: 3.12 (2H, s), 6.43 (1H, s), 7.99 (1H, brs).

Compound 1f: 5-Butyl-3-(2-phenylethyl)-1-[2'-[(2,4-dioxopyrrolidine-5(Z)-ylidene)methyl]biphenyl-4-yl]methyl-1H-1,2,4-triazole Yield 32% (from compound 9), m.p.188 to 189° C., sand like crystals (from ethanol), elementary analysis: $C_{32}H_{32}N_4O_2$; Calculated: C: 76.17, H: 6.39, N: 11.10, Found: C: 76.27, H: 6.35, N: 11.09; $^1$H-NMR (500 MHz, CDCl$_3$) data; 3,5 substituent of triazole: 0.91 (3H, t, J=7.6 Hz), 1.37 (2H, qt, J=7.6 Hz), 1.69 (2H, tt, J=7.6 Hz), 2.70 (2H, t, J=7.6), 2.99–3.22 (4H, m), 7.14–7.47 (5H, m); Biphenyl methyl group: 5.28 (2H, s), 7.14–7.47 (8H, m); Dioxopyrrolidine group: 3.12 (2H, s), 6.43 (1H, s), 8.16 (1H, s).

Compound 1g: 5-Butyl-3-(4-fluorophenyl)-1-[2'-[(2,4-dioxopyrrolidine-5(Z)-ylidene)methyl]biphenyl-4-yl]methyl-1H-1,2,4-triazole Yield 33% (from compound 9), m.p.188 to 190° C., needle like crystals (from ethyl acetate/hexane), elementary analysis: $C_{30}H_{27}N_4O_2F$; Calculated: C; 72.86, H; 5.50, N: 11.33, Found: C: 72.77, H; 5.35, N; 11.36; $^1$H-NMr (500 MHz, CDCl$_3$) data; 3,5 substituent of triazole: 0.92 (3H, t, J=7.6 Hz), 1.41 (2H, qt, J=7.6 Hz), 1.73 (2H, tt, J=7.6 Hz), 2.76 (2H, t, J=7.6 Hz), 7.21 (2H, t, J=8.7 Hz), 8.09 (2H, dd, J=5.7, 5.5 Hz); Biphenyl methyl group: 5.39 (2H, 9), 7.24 (2H, d, J=8.2 Hz), 7.31 (2H, d, J=8.2 Hz), 7.39–7.44, (4H, m); Dioxopyrrolidine group: 3.12 (2H, s), 6.43 (1H, s), 8.10 (1H, s).

Compound 1h: 5-Butyl-3-(2-fluorophenyl)-1-[2'-[(2,4-dioxopyrrolidine-5(Z)-ylidene)methyl]biphenyl-4-yl]methyl-1H-1,2,4-triazole Yield 22% (from compound 9), m.p.169 to 170° C., sand like crystals (from ethyl acetate/hexane), elementary analysis: $C_{30}H_{27}N_4O_2F$; Calculated: C: 72.06, H: 5.50, N: 11.33, Found: C: 72.75, H: 5.47, N: 11.34; $^1$H-NMR (500 MHz, CDCl$_3$) data; 3,5 substituent of triazole: 0.92 (3H, t, J=7.4 Hz), 1.41 (2H, qt, J=7.4 Hz), 1.73 (2H, tt, J=7.4 Hz), 2.78 (2H, t, J=7.4 Hz), 7.13–7.47 (3H, m), 8.06 (1H, td, J=7.6, 2.0); Biphenyl methyl group: 5.44 (2H, s), 7.13–7.47 (8H, m); Dioxopyrrolidine group: 3.11 (2H, s), 6.42 (1H, s), 8.10 (1H, s).

Compound 1i: 5-Butyl-3-(pyridine-4-yl)-1-[2'-[(2,4-dioxopyrrolidine-5(Z)-ylidene)methyl]biphenyl-4-yl]methyl-1H-1,2,4-triazole Yield 13% (from compound 9), m.p.144 to 145° C., needle like crystals (from ethyl acetate/hexane), elementary analysis: $C_{29}H_{27}N_5O_2$, Calculated: C: 72.94, H: 5.70, N: 14.66, Found: C: 72.65, H: 5.80, N: 14.41; $^1$H-NMR (500 MHz, CDCl$_3$) data; 3,5 substituent of triazole: 0.92 (3H, t, J=7.7 Hz), 1.40 (2H, qt, J=7.7 Hz), 1.72 (2H, tt, J=7.7 Hz), 2.78 (2H, t, J=7.7 Hz), 7.99 (2H, d, J=5.3 Hz), 8.68 (2H, d, J=5.3 Hz); Biphenyl methyl group: 5.44 (2H, s), 7.26 (2H, d, J=7.9 Hz), 7.35–7.42 (5H, m), 7.53 (1H, d, J=7.3 Hz); Dioxopyrrolidine group: 3.80 (2H, s), 6.14 (1H, s).

Compound 1j: 5-Butyl-3-(furan-2-yl)-1-[2'-[(2,4-dioxopyrrolidine-5(Z)-ylidene)methyl]biphenyl-4-yl]methyl-1H-1,2,4-triazole Yield 30% (from compound 9), m.p.169 to 170° C., sand like crystals (from ethyl acetate/hexane), elementary analysis: $C_{28}H_{26}N_4O_3$; Calculated: C: 72.08, H: 5.62, N: 12.01, Found: C: 72.07, H: 5.57, N: 12.13; $^1$H-NMR (500 MHz, CDCl$_3$) data;

3,5 substituent of triazole: 0.91 (3H, t, J=7.6 Hz), 1.39 (2H, qt, J=7.6 Hz), 1.72 (2H, tt, J=7.6 Hz), 2.76 (2H, t, J=7.6 Hz), 6.50 (1H, dd, J=3.4, 1.8 Hz), 6.97 (1H, dd, J=3.4, 0.9 Hz), 7.51 (1H, dd, J=1.8, 0.9 Hz); Biphenyl methyl group: 5.40 (2H, s), 7.24 (2H, d, J=8.1 Hz), 7.30 (2H, d, J=8.1 Hz), 7.37–7.48 (4H, m); Dioxopyrrolidine group: 3.12 (2H, s), 6.42 (1H, s), 8.33 (1H, s).

Compound 1k: 5-Butyl-3-(thiophene-2-yl)-1-[2'-[(2,4-dioxopyrrolidine-5(Z)-ylidene)methyl]biphenyl-4-yl]methyl-1H-1,2,4-triazole Yield 37% (from compound 9), m.p.186 to 187° C., sand like crystals (from ethyl acetate), elementary analysis: $C_{28}H_{26}N_4O_2S$; Calculated: C: 69.69, H: 5.43, N: 11.61, Found: C: 69.39, H: 5.40, N: 11.68; $^1$H-NMR (500 MHz, CDCl$_3$) data; 3,5 substituent of triazole: 0.91 (3H, t, J=7.4 Hz), 1.39 (2H, qt, J=7.4 Hz), 1.71 (2H, tt, J=7.4 Hz), 2.75 (2H, t, J=7.4 Hz), 7.09 (1H, dd, J=5.2, 3.5 Hz), 7.22–7.45 (1H, m), 7.68 (1H, dd, J=3.5, 1.1 Hz); Biphenyl methyl group; 5.38 (2H, s), 7.22–7.45 (8H, m); Dioxopyrrolidine group: 3.12 (2H, s), 6.42 (1H, s), 8.12 (1H, s).

EXAMPLE 2

Synthesis of the Present Compound 2d: 3,5-Dibutyl-1-[2'-[4-hydroxy-2(5H)-furanone-5(Z)-ylidene)methyl]biphenyl-4-yl]methyl-1H-1,2,4-triazole Compound 9d (1.55 g, 4.13 mmol) and 4-methoxy-2 (5H)-furanon (compound 12) (0.52 g, 4.56 mmol) were dissolved in absolute ethyl alcohol (6.5 ml), and 0.1 N LiOH (4 ml) was added to the solution. Then, the solution was stirred at room temperature for three hours, ethyl alcohol was distilled off therefrom under reduced pressure, and ethylacetate (100 ml×2) was added to the residue for extraction. The extract was washed with water (50 ml×2) and dried over magnesium sulfate. The solvent was then condensed under reduced pressure to obtain an aldol reaction product (compound 13d), which was a white solid. Compound 13d was dissolved in CH$_2$Cl$_2$ anhydride (80 ml). MeSO$_2$Cl (0.33 ml, 4.3 mmol), dimethylaminopyridine (0.47 g, 3.9 mmol) and triethylamine (1.10 ml, 7.89 mmol) were added to the solution, while stirring and cooling to –50° C., and the temperature of which was gradually increased to −16° C. in 1 hour. Then water (40 ml) was added to the reaction liquid to separate an organic phase, washed with saturated brine (50 ml×2) and the mixture was then dried over magnesium sulfate and condensed under reduced pressure to obtain an O-mesylated form of compound 13d. The O-mesylated form was dissolved in anhydrous $CH_2Cl_2$ (80 ml), and DBU (1.20 ml, 8.02 mmol) was added to the solution, which was then heater and refluxed for 20 minutes. After cooling, water (40 ml) was added to the solution to separate an organic phase, which was then washed with saturated brine (50 ml) and water (30 ml), dried over magnesium sulfate, and then condensed under reduced pressure. The results of $^1$H-NMR indicated that the ratio of compound 14d to its (E)-isomer in the residue was 92:8. The residue was subjected to column chromatography (silica gal, 200 g, hexane/ethyl acetate=2:3) to obtain a white solid 14d (1.59 g; 82% from 9d). Ethyl acetate-hexane was used for recrystallization to obtain colorless plate like crystals with a melting point of 89.5 to 90.5° C. The physical property values of compound 14d are shown below.

Rf=0.17 (hexane/ethyl acetate=2:3), IR(KBr): 1759 cm$^{-1}$: $^1$H-NMR (500 MHz, CDCl$_3$) δ: 0.88, 0.94 (each 3H, t, J=7.6 Hz, Me), 1.35, 1.40 (each 2H, qt, J=7.6 Hz, CH$_2$Me), 1.66, 1.74 (each 2H, tt, J=7.6 Hz, CH$_2$Et), 2.70, 2.72 (each 2H, t, J=7.6 Hz, CH$_2$Pr), 3.88 (3H, s, OMe), 5.24 (1H, s, H-3"), 5.32 (2H, s, N$_1$—CH$_2$), 6.19 (1H, s, 5"=CH), 7.18 (2H, d, J=8.1 Hz, ArH-3, 5), 7.28 (1H, dd, J=7.6, 1.6 Hz, ArH-6'), 7.31 (2H, d, J=8.1 Hz, ArH-2, 6), 7.36 (1H, ddd, J=7.6, 7.6, 1.4 Hz, ArH-5'), 7.41 (1H, ddd, J=7.7, 7.6, 1.6 Hz, ArH-4'), 8.23 (1H, dd, J=7.7, 1.4 Hz, ArH-3').

An (E)-isomer of compound 14d had a yield of 7% and Rf=0.27 (hexane/ethyl acetate=2:3 , and $^1$H-NMR showed that the peak of-ylidene-H moved to low magnetic fields (0.4 PPM). The E/Z ratios of other compounds 14a to 14c and 14e to 14k obtained by dehydrating the aldol reaction product (compound 13) in two steps are shown below: compound 14a=94:6, compound 14b=94:6, compound 14c=100:0, compound 14e=93:7, compound 14f=98:2, compound 14g=97:3, compound 14h=94:6, compound 14i=94:6, compound 14j=89:11, compound 14k=94:6.

Under a nitrogen atmosphere, compound 14d (1.249, 2.63 mmol) was dissolved in anhydrous DMPU (6 ml), and the solution was cooled in ice and stirred, and a 0.36 M DMPU solution of n-PrSLi (15 ml, 5.40 mmol) was added. The reaction liquid was stirred at room temperature for 0.5 hour, and water (100 ml) was added thereto under cooling in ice, and then, the liquid was washed with ethyl acetate (50 ml). The aqueous phase was rendered acidic (pH=2) with 10% hydrochloric acid, and ethyl acetate (50 ml×2) was used for extraction. The extract was washed with water (50 ml×3) and dried over sodium sulfate. The solvent was distilled off under reduced pressure to obtain compound (Z) 2d (0.92 g, 77%) as a white solid. Ethyl acetate was used for recrystallization to obtain colorless plate like crystals with a melting point of 168 to 169° C. The physical property values of compound 2d are shown below.

IR (KBr): 3411, 1767, 1601 cm$^{-1}$; (CHCl$_3$): 1752, 1598 cm$^{-1}$, $^1$H-NMR (300 MHz, CDCl$_3$) δ: 0.70, 0.90 (each 3H, t, J=7.5 Hz, Me), 1.20, 1.35 (each 2H, qt, J=7.5 Hz, CH$_2$Me), 1.47, 1.67 (each 2H, tt, J=7.5 Hz, CH$_2$Et), 2.64, 2.68 (each 4H, m, CH$_2$Pr), 4.98 (1H, s, H-3"), 5.33 (2H, s, N$_1$—CH$_2$), 6.24 (1H, s, 5"=CH), 7.25–7.47 (7H, m, ArH-2,3,5,6,4',5', 6'), 8.33 (1H, dd, J=7.7, 1.1 Hz, ArH-3');

Elementary analysis: C$_{28}$H$_{31}$N$_3$O$_3$; Calculated: C: 73.50, H: 6.83, N: 9.18: Found: C: 73.43, H: 6.73, N; 9.27.

In addition, when compound (E)-14d was O-demethylated as described above, it was isomerized to obtain only compound (Z) 2d.

Other 1-[2'-[(4-hydroxy-2(5H) -furanone-5(Z)-ylidene) methyl]biphenyl-4yl]methyl-1H-1,2,4-triazole compounds 2a, 2b, 2c, 2e, 2f, 2g, 2h, 2j, and 2k were obtained in the same manner as described above. Their yields and physical property values are shown below.

Compound 2a: 3,5-Dipropyl-1-[2'-[(4-hydroxy-2 (5H)-furanone-5(Z)-ylidene)methyl]biphenyl-4-yl] methyl-1H-1,2,4-triazole Yield 40% (from compound 9), m.p.160 to 161° C., plate like crystals (from ethyl acetate), elementary analysis: C$_{26}$H$_{27}$N$_3$O$_3$; Calculated: C: 72.71, H: 6.34, N: 9.78, Found: C: 72.65, H: 6.21, N: 9.52; $^1$H-NMR (300 MHz, CDCl$_3$) data; 3,5 substituent of triazole: 0.74, 0.93 (each 3H, t, J=7.5 Hz), 1.51, 1.72 (each 2H, qt, J=7.5 Hz), 2.64, 2.65 (each 2H, t, J=7.5 Hz); Biphenyl methyl group: 5.34 (2H, s), 7.28–7.47 (7H, m), 8.33 (1H, d, J=8.2 Hz); Tetronic acid group: 4.96 (1H, s), 6.21 (1H, s).

Compound 2b: 3,5-Diisopropyl-1-[2'-[(4-hydroxy-2 (5H)-furanone-5(Z)-ylidene)methyl]biphenyl-4-yl] methyl-1H-1,2,4-triazole Yield 20% (from compound 9), m.p.191 to 193° C., plate like crystals (from ethyl alcohol), elementary analysis: C$_{26}$H$_{27}$N$_3$O$_3$; Calculated; C: 72.71, H: 6.34, N: 9.78, Found: C: 72.63, H: 6.27 N: 9.73; $^1$H-NMR (500 MHz, CDCl$_3$) data; 3,5 substituent of triazole: 1.07, 1.28 (each 6H, d, J=6.9 Hz), 2.98, 3.05 (each 1H, qq, J=6.9 Hz); Biphenyl methyl group: 5.37 (2H, s), 7.27 (2H, d, J=8.2 Hz), 7.31–7.45 (5H, m), 8.32 (1H, d, J=8.2 Hz); Tetronic acid group: 4.89 (1H, s), 6.15 (1H, s).

Compound 2c: 5-Butyl-3-cyclopropyl-1-[2'-[(4-hydroxy-2(5H)-furanone-5(Z)-ylidene)methyl] biphenyl-4-yl]methyl-1H-1,2,4-triazole Yield 31% (from compound 9), m.p.168 to 170° C., plate like crystals (from ethyl acetate), elementary analysis: C$_{27}$H$_{27}$N$_3$O$_3$; Calculated: C: 73.45, H: 6.16, N: 9.52, Found: C: 73.35, H: 6.26, N: 9.41; $^1$H-NMR (300 MHz, CDCl$_3$) data; 3,5 substituent of triazole: 0.71 (3H, J=7.4 Hz), 0.95 (2H, m), 1.23 (2H, qt, J=7.4 Hz), 1.46 (2H, tt, J=7.4 Hz), 1.90–1.97 (1H, m), 2.63 (2H, t, J=7.4 Hz); Biphenyl methyl group: 5.29 (2H, s), 7.25–7.47 (7H, m), 8.32 (1H, d, J=7.1 Hz); Tetronic acid group: 5.03 (1H, s), 6.23 (1H, s).

Compound 2e: 5-Butyl-3-phenyl-1-[2'-[(4-hydroxy-2(5H)-furanone-5(Z)-ylidene)methyl]biphenyl-4-yl] methyl-1H-1,2,4-triazole Yield 22% (from compound 9), m.p.188 to 189° C., needle like crystals (from ethyl acetate), elementary analysis: C$_{30}$H$_{27}$N$_3$O$_3$; Calculated: C: 75.45, H: 5.70, N: 8.90, Found: C: 75.18, H: 5.78, N: 8.96; $^1$H-NMR (300 MHz, CDCl$_3$) data; 3.5 substituent of triazole: 0.68 (3H, t, J=7.4 Hz), 1.24 (2H, qt, J=7.4 Hz), 1.49 (2H, tt, J=7.4 Hz), 2.70 (2H, t, J=7.4 Hz), 7.30–7.47 (3H, m), 7.91–7.95 (2H, m); Biphenyl methyl group: 5.44 (2H, s), 7.30–7.47 (7H, m), 8.33 (1H, d, J=8.2 Hz); Tetronic acid group: 4.91 (1H, s), 6.27 (1H, s);

Compound 2f: 5-Butyl-3-(2-phenylethyl)-1-[2'-[(4-hydroxy-2(5H)-furanone-5(Z)-ylidene)methyl] biphenyl-4-yl]methyl-1H-1,2,4-triazole Yield 31% (from compound 9), m.p.184 to 185° C., sand like crystals (from ethanol), elementary analysis:

$C_{32}H_{31}N_3O_3$; Calculated: C: 76.02, H: 6.18, N: 8.31, Found: C: 75.88, H: 6.06, N: 8.33; $^1$H-NMR (300 MHz, CDCl$_3$) data; 3,5 substituent of triazole: 0.99 (3H, t, J=7.5 Hz), 1.35 (2H, qt, J=7.5 Hz), 1.66 (2H, tt, J=7.5 Hz), 2.71 (2H, t, J=7.5 Hz), 2.96–3.11 (4H, m), 7.12–7.44 (5H, m); Biphenyl methyl group: 5.33 (2H, s), 7.12–7.44 (7H, m), 8.20 (1H, dd, J=9.5, 1.4 Hz); Tetronic acid group: 5.14 (1H, s), 6.24 (1H, s).

Compound 2g: 5-Butyl-3-(4-fluorophenyl)-1-[2'-[(4-hydroxy-2(5H)-furanone-5(Z)-ylidene)methyl] biphenyl-4-yl]methyl-1H-1,2,4-triazole Yield 21% (from compound 9), m.p.175 to 176° C., plate like crystals (from ethyl acetate/hexane), elementary analysis: $C_{30}H_{26}N_3O_3F$; Calculated: C: 72.71, H: 5.29, N: 8.40, Found: C: 72.84, H: 5.29, N: 8.53; $^1$H-NMR (300 MHz, CDCl$_3$) data; 3,5 substituent of triazole: 0.70 (3H, t, J=7.5 Hz), 1.22 (2H, qt, J=7.5 Hz), 1.50 (2H, tt, J=7.5 Hz), 2.71 (2H, t, J=7.5 Hz), 7.08 (2H, t, J=8.7 Hz), 7.92 (2H, dd, J=8.7, 5.6 Hz); Biphenyl methyl group: 5.43 (2H, s), 7.47 (7H, m), 8.31 (1H, dd, J=7.1, 1.1 Hz); Tetronic acid group: 4.92 (1H, s), 6.26 (1H, s).

Compound 2h: 5-Butyl-3-(3-fluorophenyl)-1-[2'-[(4-hydroxy-2(5H)-furanone-5(Z)-ylidene)methyl] biphenyl-4-yl]methyl-1H-1,2,4-triazole Yield 23% (from compound 9), m.p.184 to 185° C., needle like crystals (from ethyl acetate), elementary analysis: $C_{30}H_{24}N_3O_3F$; Calculated: C: 72.71, H: 5.29, N: 8.48, Found: C: 72.41, H: 5.15, N: 8.56; $^1$H-NMR (300 MHz, CDCl$_3$) data; 3,5 substituent of triazole: 0.70 (3H, t, J=7.6 Hz), 1.23 (2H, qt, J=7.6 Hz), 1.52 (2H, tt, J=7.6 Hz), 2.73 (2H, t, J=7.6 Hz), 7.13–7.46 (3H, m), 7.85 (1H, td, J=7.4, 1.5 Hz); Biphenyl methyl group: 5.47 (2H, s), 7.13–7.46 (7H, m), 8.31 (1H, dd, J=7.1, 1.1 Hz); Tetronic acid group: 4.38 (1H, s), 6.24 (1H, s).

Compound 2j: 5-Butyl-(furan-2-yl)-1-[2'-[(4-hydroxy-2(5H)-furanone-5(Z)-ylidene)methyl] biphenyl-4-yl]methyl-1H-1,2,4-triazole Yield 10% (from compound 9), m.p.172 to 173° C., sand like crystals (from ethanol), elementary analysis: $C_{28}H_{25}N_3O_4$; Calculated: C: 71.93, H: 5.39, N: 8.99, Found: C: 71.79, H: 5.36, N: 9.03; $^1$H-NMR (300 MHz, CDCl$_3$) data; 3,5 substituent of triazole: 0.90 (3H, t, J=7.6 Hz), 1.38 (2H, qt, J=7.6 Hz), 1.71 (2H, tt, J=7.6 Hz), 2.79 (2H, t, J=7.6 Hz), 6.53 (1H, dd, J=3.5, 1.6 Hz), 6.94 (1H, d, J=3.5 Hz), 7.53 (1H, d, J=1.5 Hz); Biphenyl methyl group: 5.45 (2H, s), 7.28–7.43 (7H, m), 8.20 (1H, dd, J=7.7, 1.7 Hz); Tetronic acid group: 5.14 (1H, s), 6.23 (1H, s), 12.01 (1H, s).

Compound 2k: 5-Butyl-3-(thiophene-2-yl)-1-[2'-[(4-hydroxy-2(5H)-furanone-5(Z)-ylidene)methyl] biphenyl-4-yl]methyl-1H-1,2,4-triazole Yield 27% (from compound 9), m.p.179 to 180° C., sand like crystals (from ethanol), elementary analysis: $C_{28}H_{25}N_3O_3S$; Calculated: C: 69.54, H: 5.21, N: 8.69, round: C: 69.27, H: 5.22, N: 8.60; $^1$H-NMR (300 MHz, CDCl$_3$) data; 3,5 substituent of triazole: 0.90 (3H, t, J=7.6 Hz), 1.39 (2H, qt, J=7.6 Hz), 1.69 (2H, qt, J=7.6 Hz), 2.77 (2H, t, J=7.6 Hz), 7.10 (1H, dd, J=5.2, 3.6 Hz), 7.27–7.43 (1H, m) 7.66 (1H, dd, J=3.6, 1.1 Hz); Biphenyl methyl group: 5.42 (2H, s), 7.27–7.43 (7H, m), 8.22 (1H, dd, J=7.4, 1.4 Hz); Tetronic acid group: 5.14 (1H, s), 6.24 (1H, s) 11.90 (1H, s).

REFERENCE EXAMPLE 4

Synthesis of the Intermediate Compound 17 3,5-Dibutyl-1-(2'-cyanobiphenyl-4-yl)methyl-4H-1,2,4-triazole Under a nitrogen atmosphere, a hydrochloride of compound 4d (2.99 g, 18.1 mmol) was dissolved in absolute ethyl alcohol (30 ml). Absolute ethyl alcohol (70 ml) of compound 3d (2.16 g, 18.6 mmol) was added dropwise to the solution over 15 minutes, while stirring and cooling at −10° C., and then the temperature was increased to 0° C. The solution was capped and stored at 5° C. for 3 days. The precipitate was filtered and condensed under reduced pressure. The residue was subjected to column chromatography (silica gel, 80 g; ethyl acetate) to obtain a white solid compound 15 (2.90 g, 70%). Rf=0.21 (ethyl acetate).

Under a nitrogen atmosphere, compound 15 (2.01 g, 8.81 mmol) was dissolved in absolute ethyl alcohol (20 ml), and compound 16 (1.41 g, 6.78 mmol) was added to the solution, which was then heated at 45 to 50° C. for 2 hours and then at 70° C. for 21 hours. The reaction liquid was condensed under reduced pressure, and the residue was subjected to column chromatography (silica gel, 80 g; ethyl acetate/methanol=10:1) to obtain compound 17 (2.20 g, 87%), which was colorless and oily.

Rf=0.23 (ethyl acetate/methanol=10:1), IR (neat): 2224 cm$^{-1}$, $^1$H-NMR (500 MHz, CDCl$_3$) δ: 0.89 (6H, t, J=7.6 Hz, Me), 1.38 (4H, qt, J=7.6 Hz, CH$_2$Me), 1.70 (4H, tt, J=7.6 Hz, CH$_2$Et), 2.65 (4H, t, J=7.6 Hz, CH$_2$Pr), 5.11 (2H, s, N$_1$—CH$_2$), 7.00 (2H, d, J=8.3 Hz, ArH-3, 5), 7.47 (1H, td, J=7.6, 1.2 Hz, ArH-4'), 7.48 (1H, dd, J=7.6, 1.2 Hz, ArH-6'), 7.55 (2H, d, J=8.3 Hz, ArH-2, 6), 7.66 (1H, td, J=7.6, 1.5 Hz, ArH-5'), 7.70 (1, dd, J=7.6, 1.5 Hz, ArH-3');

Elementary analysis: $C_{24}H_{28}N_4$; Calculated: C: 77.38, H: 7.58, N: 15.04; Found: C: 77.44, H: 7.87, N: 15.28.

EXAMPLE 3

Synthesis of the Present Compound 19a: 3,5-Dibutyl-1-[2'-[(2,4-dioxopyrrolidine-5(z)-ylidene) methyl]biphenyl-4-yl]methyl-4H-1,2,4-triazole Under a nitrogen atmosphere, compound 17 (480 mg, 1.29 mmol) was dissolved in anhydrous CH$_2$Cl$_2$. Then, 0.98 M hexane solution of iso-Bu$_2$AlH (3.46 ml, 3.22 mmol) was add dropwise to mixtures while stirring and cooling at −80° C., and 1 hour later, the reaction liquid was poured into a mixture of acetic acid (2.5 ml) and ice (3.4 g), to which 1N HCl (4.2 ml) was then added. After stirring the mixture for 4 hours, the organic phase was separated, washed with saturated aqueous NaHCO$_3$ solution (40 ml×2) and saturated brine (40 ml×2), dried over magnesium sulfate, and condensed under reduced pressure. The residue was subjected to column chromatography (silica gel, 16 g; ethyl acetate/methanol=10:1) to obtain compound 18, which was colorless and oily. The physical property values of compound 18 are shown below.

Rf=0.39 (ethyl acetate/methanol=10:1), IR (neat): 1693 cm$^{-1}$, $^1$H-NMR (500 MHz, CDCl$_3$) δ: 0.87 (6H, J=7.6 Hz, Me), 1.37 (4H, qt, J=7.6 Hz, CH$_2$Me), 1.70 (4H, tt, J=7.6 Hz, CH$_2$Et), 2.65 (4H, t, J=7.6 Hz, CH$_2$Pr), 5.12 (2H, s, N$_1$—CH$_2$), 7.05 (2H, d, J=7.9 Hz, ArH-3, 5), 7.36 (2H, d, J=7.9 Hz, ArH-2, 6), 7.39 (1H, dd, J=7.5, 0.5 Hz, ArH-6'), 7.51 (1H, td, T=7.51 0.5 Hz, ArH-4'), 7.64 (1H, t, J=7.5 Hz, ArH-5'), 8.01 (1H, d, J=7.5 Hz, ArH-3'), 9.93 (1H, s, CHO).

HBr was used to O-demethylate aldol reaction product obtained by reacting compound 18 (570 mg, 1.54 mmol)

with compound 10 (440 mg, 3.85 mmol), as in the reaction through which compound 1d was obtained from compound 9d. Compound 19a was obtained as light-yellow needle like crystals at a yield of 33% by recrystallization from AcOEt/iso-Pr$_2$O. m.p.185 to 186° C., Rf=0.15 (ethyl acetate/methanol=10:1), IR (KBr): 3206, 1682 cm$^{-1}$; $^1$H-NMR (500 MHz, CDCl$_3$) δ: 0.87 (6H, t, J=7.6 Hz, Me), 1.39 (4H, qt, J=7.6 Hz, CH$_2$Me), 1.71 (4H, tt, J=7.6 Hz, CH$_2$Et), 2.65 (4H, t, J=7.6 Hz, CH$_2$Pr), 3.13 (2H, s, CH$_2$-3"), 5.10 (2H, s, N$_1$—CH$_2$), 6.39 (1H, s, 5"=CH), 6.99 (2H, d, J=8.3 Hz, ArH-3, 5), 7.30 (2H, d, J=8.3 Hz, ArH-2, 6), 7.40–7.48 (4H, m, ArH-3', 4', 5', 6'), 8.09 (1H, s, NH), elementary analysis: C$_{28}$H$_{32}$N$_4$O$_2$; Calculated: C: 73.66, H: 7.06, N: 12.27; Found: C: 73.79, H: 6.98, N: 12.23.

EXAMPLE 4

Synthesis of the Present Compound 19b: 3,5-Dibutyl-1-[2'-[(4-hydroxy-2(5H)-furanone-5(Z)-ylidene)-methyl]biphenyl-4-yl]methyl-4H-1,2,4-triazole Compound 19b was obtained by reacting compound 18 with compound 12 at a yield of 20%, using the reaction through which compound 2d was obtained from compound 9d. White needle like crystals were obtained by recrystallization: from AcOEt/CH$_2$Cl$_2$. m.p.166to 168° C., IR (KBr): 1760 cm$^{-1}$; $^1$H-NMR (300 MHz, CDCl$_3$) δ: 0.83 (6H, t, J=7.5 Hz, Me), 1.34 (4H, qt, J=7.5 Hz, CH$_2$Me), 1.65 (4H, tt, J=7.5 Hz, CH$_2$Et), 2.69 (4H, t, J=7.5 Hz, CH$_2$Pr), 5.13 (2H, s, N$_1$—CH$_2$), 5.29 (1H, s, H-3"), 6.17 (1H, s, 5"=CH), 7.08 (2H, d, J=8.2 Hz, ArH-3, 5), 7.30 (1H, dd, J=7.5, 1.4 Hz, ArH-6'), 7.36 (1H, td, J=7.5, 1.4 Hz, ArH-4'), 7.41 (2H, d, J=8.2 Hz, ArH-2, 6), 7.43 (1H, td, J=7.5, 1.5 Hz, ArH-5'), 8.32 (1H, dd, J7.5, 1.5 Hz, ArH-3'), elementary analysis: C$_{28}$H$_{31}$N$_3$O$_3$; Calculated: C: 73.50, H: 6.83, N: 9.18; Found: C: 73.54, H: 6.76, N: 9.98.

DRUG TEST EXAMPLES

Test Example 1: The Effect of Binding Inhibition of Angiotensin II to Angiotensin II Receptor The method of Cox et. al (Biochemical Pharmacology 33, 4057–4064 (1984) was modified to conduct angiotensin II receptor binding inhibition experiments. The present compounds (10$^{-5}$M to 10$^{-9}$M) and $^3$H labeled angiotensin II (10$^{-9}$M) were added to a fraction of angiotensin II receptor membrane (0.57 m/ml) prepared from rabbit adrenal gland and were allowed to react in a 20 mM Tris HCl buffer (pH: 7.0) containing 120 mM NaCl, 5 mM EDTA, 0.1 mM PMSF, and 0.2% BSA at 30° C. for 20 minutes so that the final volume was 540 μl. Then, the reaction mixture was quickly passed through a filter (whatman GF/B), and the filter was then rinsed three times in 4 ml of the buffer cooled in ice. Then, the radioactivity of receptor binding $^3$H labeled angiotensin II captured on the filter was measured using a liquid scintillation counter. The angiotensin II receptor binding inhibition activity of the present compounds was evaluated based on the concentration (IC 50) required to replace 50% of the total amount of specifically binding $^3$H labeled angiotensin II. The results are shown in Table 1.

Test Example 2: Inhibition Effects of Compounds in Vascular Contraction Caused by Angiotensin II Using Pieces of the Aortae of Guinea Pigs Male Hartly guinea pigs (350 to 400 g) were contused on the head and sacrificed by allowing their blood to discharge from the arteria carotis communis. Immediately after death, the chest aorta was removed. A spiral sample of width 2 to 3 mm and length 20 to 25 mm was cut from the aorta, and was suspended in 4.5 ml of Krebs-Henseleit (K-H) solution (120 mM NaCl, 4.7 mM KCl, 4.7 mM MgSO$_4$, 1.2 mM KH$_2$PO$_4$, 2.5 mM CaCl$_2$, 25 mM NaHCO$_3$, and 10 mM glucose) in a Magnus vessel. The K-H solution in the Magnus vessel was maintained at 37° C., and a mixture gas of 95% O$_2$ and 5% CO$_2$ was continuously bubbled through the solution. First, 1 g of initial tension was applied to the sample, which was then left to stand rest for about 30 minutes, and 45 μl of 4M KCl solution was added to the solution to induce contraction. After contraction had stabilized, a washing operation was performed to replace the K-H solution. Then, after the sample was left to stand for 30 minutes, 45 μl of solvent DMSO was added to incubate the sample for 15 minutes, and 45 μl of angiotensin II solution (3×10$^{-8}$M) was added to induce contraction. This operation was repeated three times and 100% contraction was used as the average. Subsequently, the sample was stabilized by washing. Then, a 45 μl sample of each test compound prepared for each concentration (3×10$^{-5}$M to 10$^{-7}$M) using DMSO as a solvent was used to observe the inhibition effect of angiotensin II on vascular contraction by performing the same operation as described above. The contraction reaction was recorded on a recorder (RTA-1100, Japan Photoelectronics) via an equi-scale pressure transducer (TB-651T, Japan Photoelectronics). The angiotensin II inhibition effects of the test compounds were evaluated using the IC50 value. The results are shown in Table 1.

Test Example 3: Inhibition Effect of Compounds in the Hypertension Caused by Angiotensin II Using Rats Male SD rats (age; 11 weeks; 310 to 330 g) Were used, and indwelling cannula were placed in the femoral aorta and the vena cava, under anesthesia with inactin. The arterial cannula was connected to a pressure transducer to record the blood pressure via a carrier amplifier (AP-601G Japan Photoelectronics) using a polygraph system (RM-6000 Japan Photoelectronics). Prior to tests using the test compounds, 100 ng/kg-equivalent angiotensin II (50 μl of serum solution from the rat) was administered using a regular-pulse cannula to check the hypertensive action. Then, 30 minutes later, a 1 mg/kg-equivalent test compound (50 μl of serum solution from the rat) was administered using the regular-pulse cannula, and similar administration of angiotensin II was performed 5 and 60 minutes later to check the corresponding hypertensive action. The hypertensive effect resulting from the administration of only angiotensin II was taken as a reference value of 100% to determine the antihypertensive rates of the test compounds. The results are shown in Table 1.

Test Example 4: Toxicity Tests of Compounds Using Male ICR Mice

Acute toxicity tests of the compounds 1d and 2d described in table 1 were carried out. 250 mg/kg, 500 mg/kg, and 1,000 mg/kg of the compounds in a suspension contained 0.1% carboxymethylcellulose were then orally administered to five-week-old male ICR mice (weight: 24 to 32 g, 5 per group), and wherein the mice were observed for 21 days after administration. As a result, in each administration group, no mouse died whichever compound had been administered. In addition, all the mice showed a physiological weight transition, and were dissected at the end of the observation period to check that they exhibited was no abnormality.

FORMULATION EXAMPLE

Capsules 100 mg of powdered active ingredient, 150 mg of lactose, 50 mg of microcrystalline cellulose and 10 mg of magnesium stearate were mixed together, and the mixture was granulated and sealed in standard gelatin capsules to prepare capsules of each active ingredient.

Tablets 100 mg of powdered active ingredient, 100 mg of lactose, 50 mg of starch powder, 140 mg of microcrystal line cellulose and 10 mg of magnesium stearate were mixed, and the mixture was granulated. Tablets of each active ingredient were prepared according to the conventional method.

Injections 1.0 wt. % of powdered active ingredient, 10 vol. % of propyleneglycol and an appropriate amount of parenteral composition were dissolved in distilled water for injection and the solution was sealed in an ampul to prepare injections of each active ingredient. The entire process was executed under aseptic conditions.

TABLE 1

| Compound No. | Receptor binding inhibition effect $IC_{50}$ ($\mu M$) | Vascular contraction inhibition effect $IC_{50}$ ($\mu M$) | Inhibition effect in the hypertension by angiotensin II (1 mg/kg, i. v.) | |
|---|---|---|---|---|
| | | | 5 minutes after administration | 60 minutes after administration |
| 1 a | 0.22 | >300 | ++ a) | − a) |
| 1 b | >7.0 | >300 | NT a) | NT |
| 1 c | 2 | >300 | NT | NT |
| 1 d | 0.13 | 1.4 | +++ a) | ++ |
| 1 e | >6.3 | >300 | NT | NT |
| 1 f | 0.15 | 87.9 | ++ | ++ |
| 1 g | >6.1 | >300 | NT | NT |
| 1 h | 4.5 | >300 | NT | NT |
| 1 i | >6.3 | >300 | NT | NT |
| 1 j | 2.2 | >300 | NT | NT |
| 1 k | 4.2 | >300 | NT | NT |
| 19 a | 8 | >300 | NT | NT |
| 2 a | 0.11 | 16.9 | ++ | − |
| 2 b | 0.93 | >300 | NT | NT |
| 2 c | 0.15 | >300 | + a) | − |
| 2 d | 0.046 | 4.5 | ++ | + |
| 2 e | 0.18 | 154.1 | ++ | ++ |
| 2 f | 0.011 | >300 | ++ | − |
| 2 g | 0.69 | >300 | NT | NT |
| 2 h | 0.27 | 220 | + | − |
| 2 j | 0.28 | >300 | − | − |
| 2 k | 0.31 | >300 | + | − |
| 19 b | 0.68 | >300 | NT | NT | a) NT = not tested,
+++ ≧ 70%,
70% > ++ ≧ 30%,
30% > + ≧ 10%,
10% > −

Toxicities of the present compounds are low and safety of them is high. Based on the angiotensin II antagonism, they suppress the vascular contraction and hypertensive effects by angiotensin II, thereby reducing the blood pressure of animals, in particular, mammals such as humans, dogs, monkeys, rabbits, and rats. Thus, the present compounds are effective as therapeutic agents for hypertension and other disease caused by angiotensin II, specifically, for hypertension such as essential, renal, or renovascular hypertension and circulatory system disease including heart failure.

What is claimed is:

1. A compound of the following formula (I) or its salt:

(I)

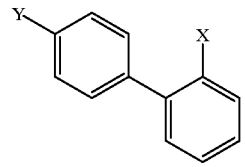

wherein X is a group of the following formula (III):

(III)

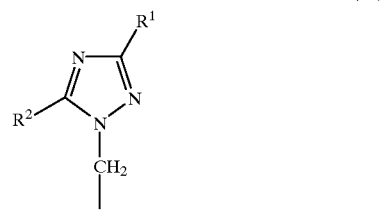

Y is a group of the following formula (IV) or (V):

(IV)

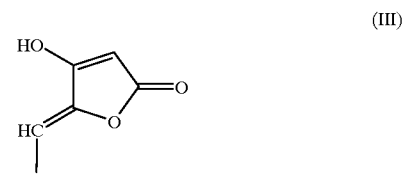

(V)

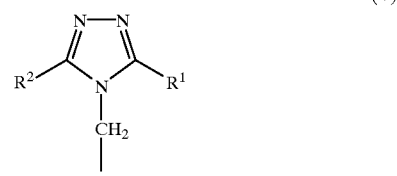

$R^1$ and $R^2$ independently represent a hydrogen atom, an alkyl group having 1 to 6 carbon atoms, a haloalkyl group having 1 to 6 carbon atoms, a cycloalkyl group having 3 to 6 carbon atoms, phenyl, 2-fluorophenyl, 4-fluorophenyl, phenylmethyl and 2-phenylethyl.

2. A compound or its salt according to claim 1, wherein in said formula (I), X is a group of the following formula (III):

(III)

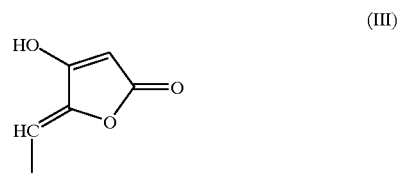

and Y is a group of the following formula (IV):

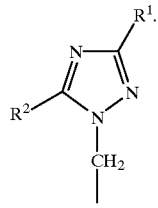
(IV)

3. A compound or its salt according to claim 1, wherein in said formula (I), X is a group of the following formula (III):

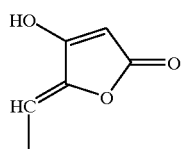
(III)

and Y is a group of the following formula (V):

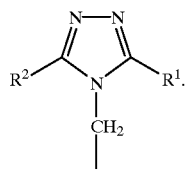
(V)

4. A medical composition containing a therapeutically effective amount of angiotensin II receptor antagonistic compound and a medically acceptable carrier and/or diluent, wherein said angiotensin II receptor antagonistic compound is selected from a compound of the formula (I) according to claim 1 or its medically acceptable salt.

5. A compound or its salt according to claim 1, wherein $R^1$ and $R^2$ independently represent a hydrogen atom, an alkyl group having 1 to 6 carbon atoms, a haloalkyl group having 1 to 6 carbon atoms, a cycloalkyl group having 3 to 6 carbon atoms, phenyl, 2-fluorophenyl, 4-fluorophenyl and 2-phenylethyl.

* * * * *